US011230705B2

(12) United States Patent
Sanghani et al.

(10) Patent No.: US 11,230,705 B2
(45) Date of Patent: Jan. 25, 2022

(54) GENETICALLY MODIFIED ISOPROPYLMALATE ISOMERASE ENZYME COMPLEXES AND PROCESSES TO PREPARE ELONGATED 2-KETOACIDS AND $C_5$-$C_{10}$ COMPOUNDS THEREWITH

(71) Applicant: Dow Global Technologies LLC, Midland, MI (US)

(72) Inventors: Paresh Sanghani, Indianapolis, IN (US); Eric C. Shiue, Evanston, IL (US); Scott A. Greenwalt, Indianapolis, IN (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/650,094

(22) PCT Filed: Sep. 25, 2018

(86) PCT No.: PCT/US2018/052579
§ 371 (c)(1),
(2) Date: Mar. 24, 2020

(87) PCT Pub. No.: WO2019/067412
PCT Pub. Date: Apr. 4, 2019

(65) Prior Publication Data
US 2020/0291378 A1  Sep. 17, 2020

Related U.S. Application Data

(60) Provisional application No. 62/565,271, filed on Sep. 29, 2017.

(51) Int. Cl.
*C12N 9/88*  (2006.01)
*C12P 7/42*  (2006.01)
(52) U.S. Cl.
CPC .................. *C12N 9/88* (2013.01); *C12P 7/42* (2013.01); *C12Y 402/01033* (2013.01)
(58) Field of Classification Search
CPC ..... C12N 9/88; C12P 7/42; C12P 7/24; C12Y 203/03013
See application file for complete search history.

(56) References Cited

U.S. PATENT DOCUMENTS

| 8,232,089 | B2 | 7/2012 | Urano et al. |
| 8,298,798 | B2 | 10/2012 | Liao et al. |
| 2011/0201083 | A1 | 8/2011 | Liao et al. |
| 2012/0070868 | A1 | 3/2012 | Lee et al. |
| 2014/0377857 | A1 | 12/2014 | Liao et al. |
| 2015/0259710 | A1 | 9/2015 | Dundon et al. |
| 2016/0355850 | A1 | 12/2016 | Sanghani et al. |
| 2017/0232043 | A1 | 8/2017 | Falb et al. |
| 2017/0369863 | A1 | 12/2017 | Sanghani et al. |

FOREIGN PATENT DOCUMENTS

| WO | 2009046375 A2 | 4/2009 |
| WO | 2009096370 A1 | 8/2009 |
| WO | 2010045629 A2 | 4/2010 |
| WO | 2010150230 A1 | 12/2010 |
| WO | 2012135731 A2 | 10/2012 |
| WO | 2015089127 A1 | 6/2015 |
| WO | 2016094604 A1 | 6/2016 |

OTHER PUBLICATIONS

Office Action dated Jul. 16, 2020 pertaining to U.S. Appl. No. 16/338,098, filed Mar. 29, 2019, 19 pgs.
Devos et al., (Proteins: Structure, Function and Genetics, 2000, vol. 41: 98-107.
Whisstock et al., (Quarterly Reviews of Biophysics 2003, vol. 36 (3): 307-340.
Witkowski et al., (Biochemistry 38: 11643-11650,1999.
Kisselev L., (Structure, 2002, vol. 10: 8-9.
Notice of Allowance and Fee(s) due dated Jan. 7, 2021 pertaining to U.S. Appl. No. 16/338,098, filed Mar. 29, 2019, 14 pgs.
Atsumi et al., "Non-Fermentative Pathways for Synthesis of Branched-Chain Higher Alcohols as Biofuels", Nature, 2008, vol. 451, 86-90, Nature Publishing Group.
Becker et al., "Bio-Based Production of Chemicals, Materials and Fuels—Corynebacterium Glutamicum as Versatile Cell Factory", Current Opinion in Biotechnology, 2012, 23, 631-640, Elsevier.
Becker et al., "Systems and Synthetic Metabolic Engineering for Amino Acid Production—The Heartbeat of Industrial Strain Development", Current Opinion in Biotechnology, 2012, 23, 718-726, Elsevier.
Choi et al., "Microbial Production of Short-Chain Alkanes", Nature, 2013, 502, 571-576, Macmillan Publishers.
Datsenko et al., "One-Step Inactivation of Chromosomal Genes in *Escherichia coli* K-12 Using PCR Products", Proc. Natl. Acad. Sci. USA, 2000, 97:12, 6640-6645.
Felnagle et al., "Engineering Synthetic Recursive Pathways to Generate Non-Natural Small Molecules", Nature Chemical Biology, Jun. 2012, 518-526, vol. 8, Nature America, Inc.
Gronenberg et al., "Next Generation Biofuel Engineering in Prokaryotes", Current Opinion in Biotechnology, 2013, 17, 462-471, Elsevier.
Han et al., "Sites and Mechanisms of Aconitase Inactivation by Peroxynitrite: Modulation by Citrate and Glutathione", Biochemistry, 2005, 11986-11996, 44, American Chemical Society.

(Continued)

*Primary Examiner* — Tekchand Saidha
(74) *Attorney, Agent, or Firm* — Dinsmore & Shohl LLP

(57) ABSTRACT

Genetically modified isopropylmalate isomerase enzyme complexes (e.g., LeuCD' enzyme complexes), microbial organisms including genetically modified isopropylmalate isomerase enzyme complexes (e.g., LeuCD'), and processes for preparing $C_7$-$C_{11}$ 2-ketoacids with genetically modified isopropylmalate isomerase enzyme complexes (e.g., LeuCD'). The genetically modified isopropylmalate isomerase enzyme complexes (e.g., LeuCD' enzyme complexes), microbial organisms, and processes for preparing $C_7$-$C_{11}$ 2-ketoacids can be used to produce $C_6$-$C_{10}$ aldehydes, alkanes, alcohols, and carboxylic acids, both in vivo and in vitro.

10 Claims, 11 Drawing Sheets

Specification includes a Sequence Listing.

(56) References Cited

OTHER PUBLICATIONS

Holton et al., "Structural Characterization of a D-Isomer Specific 2-Hydroxyacid Dehydrogenase from *Lactobacillus delbrueckii* ssp. *bulgaricus*", Journal of Structural Biology, 2013, 181, 179-184, Elsevier Inc.
Hsu et al., "Leucine Biosynthesis in *Saccharomyces cerevisiae*, Purification and Characterization of b-Isopropylmalate Dehydrogenase", The Journal of Biological Chemistry, 1980, 7255-7260, vol. 255 No. 15.
Hummel, Werner, "Large-Scale Applications of NAD(P)-Dependent Oxidoreductases: Recent Developments", Tibtech, 1999, 17, 487-492, Elsevier Science Ltd.
Imada et al., "Structure of 3-Isopropylmalate Dehydrogenase in Complex with 3-Isopropylmalate at 2.0 A Resolution: the Role of Glu88 in the Unique Substrate-Recognition Mechanism", Structure, Aug. 1998, 971-982, 6, Current Biology Publications ISSN 0969-2126.
International Search Report and Written Opinion dated Mar. 18, 2015 pertaining to International Application No. PCT/US2014/069438.
International Search Report and Written Opinion pertaining to PCT/US2015/064879 dated Mar. 22, 2016.
International Search Report and Written Opinion pertaining to PCT/US2016/069430 dated Jul. 4, 2017.
International Search Report and Written Opinion pertaining to PCT/US2016/069476 dated Jul. 4, 2017.
International Search Report and Written Opinion pertaining to PCT/US2018/052579, dated Jan. 14, 2019.
Koon et al., "Crystal Structure of LeuA from *Mycobacterium tuberculosis*, a Key Enzyme in Leucine Biosynthesis", Proc. Natl. Acad. Sci. USA, 2004, 101:22, 8295-8300.
Lee et al., "Metabolic Engineering of Clostridium Acetobutylicum M5 for Highly Selective Butanol Production", Biotechnology Journal, 2009, 1432-1440, 4, Wiley-VCH Verlag GmbH & Co.
Manikandan et al., "Structural Studies on the Enzyme Complex Isopropylmalate Isomerase [LeuCD] from *Mycobacterium tuberculosis*", Proteins, 2010, 35-49, Wiley-Liss, Inc.
Marcheschi et al., "A Synthetic Recursive '+1' Pathway for Carbon Chain Elongation", ACS Chemical Biology, 2012, 689-697, 7, American Chemical Society.
Office Action pertaining to U.S. Appl. No. 15/030,616 dated Sep. 13, 2017.
Rosano et al., "Recombinant Protein Expression in *Escherichia coli*: advances and challenges", Frontiers in Microbiology, Apr. 2014, vol. 5, Article 172, pp. 1-17.
Rude et al., "New Microbial Fuels: A Biotech Perspective", Current Opinion in Microbiology, 2009, 274-281.
Sanghani et al., "Kinetic Mechanism of Human Glutathione-Dependent Formaldehyde Dehydrogenase", Biochemistry, 2000, 10720-10729, 39, American Chemical Society.
Shen et al., "A Synthetic Iterative Pathway for Ketoacid Elongation", Methods in Enzymology, 2011, 469-481, 497, Elsevier Inc.
Spaepen et al., "Characterization of Phenylpyruvate Decarboxylase, Involved in Auxin Production of Azospirillum Brasilense", Journal of Bacteriology, 2007, 189:21, 7626-7633.
Vedha-Peters et al., "Creation of a Broad-Range and Highly Stereoselective D-Amino Acid Dehydrogenase for the One-Step Synthesis of D-Amino Acids", J. Am. Chem. Soc., 2006, 128, 10923-10929, American Chemical Society.
Versees et al., "The Crystal Structure of Phenylpyruvate Decarboxylase from Azospirillum Brasilense at 1.5 A Resolution Implications for its Catalytic and Regulatory Mechanism", The FEBS Journal, 2007, 274, 2363-2375, The Authors Journal compilation.
Wang et al., "Optimization of Butanol Production from Tropical Maize Stalk Juice by Fermentation with Clostridium Beijerinckii NCIMB 8052", Bioresource Technology, 2011, 9985-9990, 102, Elsevier Ltd.
Xiong et al., "A Bio-Catalytic Approach to Aliphatic Ketones", Scientific Reports, 2012, 2:311, doi: 10.1035/srep0311.
Zhang et al., "A Synthetic Metabolic Pathway for Production of the Platform Chemical Isobutyric Acid", ChemSusChem, 2011, 4, 1068-1070 Wiley-VCH Verlag GmbH & Co.
Zhang et al., "Expanding Metabolism for Biosynthesis of Non-natural Alcohols", PNAS, Dec. 2008, 20653-20658, vol. 105 No. 52, The National Academy of Science of the USA.
Zhang et al., "Subdomain II of alpha-isopropylmalate synthase is essential for activity: inferring a mechanism of feedback inhibition", The Journal of biological chemistry 2014, 289, 27966-27978.
Office Action dated Feb. 24, 2021 pertaining to U.S. Appl. No. 16/337,072, filed Mar. 27, 2019, 29 pgs.
Sadowski, M.I. et al., "The sequence-structure relationship and protein function prediction" Current Opinion in Structural Biology, ScienceDirect, Elsevier, 19: 357-362, 2009.
Tang, S. et al., Identification of Dehalobacter reductive dehalogenases that catalyse dechlorination of chloroform, 1,1,1-trichloroethane and 1,1-dichloroethane, Philosophical Transactions of the Royal Society, 368:20120318, pp. 1-10, 2013.
Seffernick, J. et al., "Melamine Deaminase and Atrazine Chlorohydrolase: 98 Percent Identical but Functionally Different" Journal of Bacteriology, vol. 183, No. 8, pp. 2405-2410, 2001.
Branden, C. et al., Introduction to Protein Structure, Garland Publishing Inc., New York, p. 247, 1991.
Final Rejection dated Jun. 15, 2021, pertaining to U.S. Appl. No. 16/337,072.
U.S. Notice of Allowance and Fee(s) Due dated Sep. 30, 2021 pertaining to U.S. Appl. No. 16/337,072, filed Mar. 27, 2019, 16 pages.

Ecoli-LeuC  MAKTLYEKLFDAHMVYEAENETPLLYIDRHLVHEVTSPQAFDGLRAHGRPVRQPG
Ecoli-LeuC  KTFATMDHNVSTQTKDINACGEMARIQMQELIKNCKEEGVELYDLNHPYQGIVHV
Ecoli-LeuC  MGPEQGVTLPGMTIVCGDSHTAHGALAFGIGTSEVHVLATQTLKQGRAKT
Ecoli-LeuC  MKIEVQGKAAPGITAKDIVLAIGKTGSAGGTGHVVEFCGEAIRDLSMEGRMTLC
Ecoli-LeuC  NMAIEMGAKAGLVAPDETTENYVKGRLHAPKGKDFDDAVAYWKTLQTDEGATEDT
Ecoli-LeuC  VTLQAEELISPQVTWGTNPGQVISVNDNIPDPASFADPVERASAEKALAYMGLKP
Ecoli-LeuC  GIPLTEVAIDKVFIGSCTNSRIEDLRAAAEIAKGRKVAPGVQALVPGSGPVKAQ
Ecoli-LeuC  AEAEGLDKIFIEAGFEWRLPGCSMCLAMNNDRLNPGERCASTSNRNFEGRQGRGG
Ecoli-LeuC  RTHLVSPAMAAAAVTGHFEADIRNIK

FIG. 4

Ecoli-LeuD    MAEKEIKHTGLMVPLDAANVDTDAIPKQFLQKVTRTGFAAHLFNDMRFLDEKGQ

Ecoli-LeuD    QPNPDFVLNFPQYQGASILARENFGGSSREHAPWALTDYGFKVVIAPSFADIF

Ecoli-LeuD    YGNSFNNQLPVKLSDAEVDELFALVKANPGIHFDVDLEAQEVKAGEKTYRFTID

Ecoli-LeuD    AFRRHQMMNGLDSIGLTLQHDDAIAAYEAKQPAFMN

FIG. 5

GENETICALLY MODIFIED ISOPROPYLMALATE ISOMERASE ENZYME COMPLEXES AND PROCESSES TO PREPARE ELONGATED 2-KETOACIDS AND $C_5$-$C_{10}$ COMPOUNDS THEREWITH

CROSS-REFERENCE TO RELATED APPLICATIONS

This application is a National Stage Entry under 35 U.S.C. § 371 of International Patent Application No. PCT/US2018/052579, filed Sep. 25, 2018, which claims priority to U.S. Provisional Patent Application Ser. No. 62/565,271 filed Sep. 29, 2017, which are incorporated by reference herein in their entirety.

SEQUENCE LISTING

This application incorporates by reference the material in the ASCII text file "2020_03_18_Substitute_Sequence_Listing_DOW80959PA_ST25.txt" of 105,640 bytes created on Mar. 18, 2020, and filed herewith.

FIELD

The present disclosure generally relates to genetically modified isopropylmalate isomerase enzyme complexes (e.g., LeuCD' enzyme complexes), microbial organisms including genetically modified isopropylmalate isomerase enzyme complexes, and processes for preparing $C_7$-$C_{11}$ 2-ketoacids with genetically modified isopropylmalate isomerase enzyme complexes.

BACKGROUND

Concerns about the future scarcity, cost, and environmental impact of obtaining and using fossil fuels have stimulated interest in the exploitation of cheap, renewable biomass as an alternative source for both fuels and chemicals made therefrom. As crude oil prices have risen, bio-based chemicals and industrial products have become attractive alternatives to their petroleum-derived counterparts. Fermentation processes using anaerobic microbial organisms offer a promising path for converting biomass and agricultural waste into useful products, while at the same time remediating problems that may be encountered in disposal of low-value agricultural commodities and food processing byproducts/wastes. Some useful products that can be prepared from low-cost biomass feedstocks are $C_6$-$C_{10}$ aldehydes, $C_6$-$C_{10}$ alcohols, $C_6$-$C_{10}$ carboxylic acids, and $C_5$-$C_9$ alkanes, including, in particular, $C_6$-$C_{10}$ alcohols.

$C_6$-$C_{10}$ alcohols are produced using petrochemical and natural raw material processes. The petrochemical processes are based upon ethylene oligomerization. For example, the Ziegler process uses aluminum to mediate ethylene oligomerization at high pressure to generate tri-alkyl aluminum species. The tri-alkyl aluminum species are oxidized under dry air and hydrolyzed to yield a Poisson distribution of terminal alcohols ranging in length from $C_2$-$C_{26}$ (including an even number of carbon chain atoms only). Hydroformylation of olefins produced by ethylene oligomerization such as, e.g., via the Shell higher olefin process (i.e., SHOP), followed by reduction produces alcohols having an odd number of carbon chain atoms. Conversion of fatty acids of natural oils such as, e.g., palm kernel and coconut, through oleochemical transformation of hydrogenation, transesterification, and reduction is also employed to produce long chain alcohols with the bulk of the alcohols having carbon chain lengths of greater than $C_{10}$. The lack of selectivity to narrow carbon chain length distribution is a significant drawback of current production methods. Further, the Ziegler process is also imperfect in that a co-product thereof is hydrated alumina (i.e., $Al_2O_3[H_2O]_x$). Thus, identification of better and less expensive methods to produce $C_6$-$C_{10}$ alcohols, $C_5$-$C_9$ alkanes, and $C_6$-$C_{10}$ carboxylic acids is desired. However, microbial organisms often fail to produce many of the petrochemical based products at economically viable rates or yields. For example, while metabolic engineering has been extensively employed to build pathways and/or channel metabolites toward a pathway of interest, ethanol is currently the most common biochemical produced using microbial organisms. Economically viable methods for producing $C_6$-$C_{10}$ alcohols and $C_6$-$C_{10}$ carboxylic acids are being actively pursued in both the biofuel and chemical industries.

Success in production of natural amino acids by microbial fermentation has generated significant interest in utilizing amino acid biosynthetic pathways for producing chemicals of interest, including longer chain alcohols, alkanes, and carboxylic acids. Of particular interest are 2-ketoacids, which are key intermediates in amino acid biosynthesis that can be exploited in the biosynthesis of chemicals inside cells. Three enzymes within the leucine biosynthetic pathway are involved in elongating 2-ketoacids and can operate to convert 2-ketobutyrate, 2-ketoisovalerate, and/or 2-methyl-2-ketopentanoate to a longer chain 2-ketoacids. These enzymes are generally referred to, without reference to any specific microbial organism, as isopropylmalate synthase, isopropylmalate isomerase, and isopropylmalate dehydrogenase. In *E. coli* specifically, these enzymes are referred to as LeuA (GenBank: Accession No. NC 000913.3 Gene ID: 947465), LeuCD (GenBank: Accession No. NC 000913.3 Gene ID: 945076 and Gene ID: 945642), and LeuB (GenBank: Accession NO. NC 000913.3 Gene ID: 944798), respectively. The feasibility of extending the length of 2-ketoacids inside cells via engineering of the LeuA gene product of *E. coli* has expanded the range of biochemicals that can be produced from 2-ketoacids. In *E. coli*, the products of LeuABCD genes extend the length of 2-ketoacids by one carbon unit. Such extension is observed during leucine biosynthesis, in which the products of Leu-ABCD genes work together to convert 2-ketoisovalerate (a 5-carbon acid) to 2-ketoisocaproate (a 6-carbon acid). Additionally, expansion of the active site of LeuA allowed for the recursive extension of the $C_4$ ketoacid, 2-ketobutyric acid (i.e., 2-ketobutyrate), to a $C_9$ 2-ketoacid, 2-ketononanoic acid (i.e., 2-keto-nonanoate). However, continued development and engineering of LeuABCD genes is needed to allow for efficient production of $C_7$-$C_{11}$ 2-ketoacids and to avoid major bottlenecks in the later stages of the pathway used to elongate the 2-ketoacids.

Accordingly, there exist ongoing needs for economically viable and efficient methods for producing longer chain aldehydes, alkanes, alcohols, and carboxylic acids.

SUMMARY

Provided herein are genetically modified isopropylmalate isomerase enzyme complexes, such as, e.g., LeuCD' enzyme complexes, microbial organisms including genetically modified isopropylmalate isomerase enzyme complexes, and processes for preparing $C_7$-$C_{11}$ 2-ketoacids with genetically modified isopropylmalate isomerase enzyme complexes. In embodiments, genetically modified LeuCD' enzyme complexes are disclosed. The genetically modified LeuCD' enzyme complexes include (a) a genetically modified LeuC' subunit including: (1) an amino acid sequence with at least 80% homology to SEQ ID NO: 1 having a C-terminus; and (2) a C-terminal amino acid or peptide coupled to the C-terminus of the amino acid sequence of (a)(1), wherein the C-terminal amino acid is chosen from any naturally occurring amino acid, and wherein the C-terminal peptide includes an amino acid sequence: $(Xaa)_1(Xaa)_2(Xaa)_3(Xaa)_4(Xaa)_5(Xaa)_6(Xaa)_7(Xaa)_8(Xaa)_9(Xaa)_{10}$ (SEQ ID NO: 39). $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ of SEQ ID NO: 39 are each independently chosen from any naturally occurring amino acid, or are absent, provided that at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in the C-terminal peptide. The genetically modified LeuCD' enzyme complexes also include (b) a LeuD subunit including an amino acid sequence with at least 80% homology to SEQ ID NO: 2, wherein the genetically modified LeuCD' enzyme complex has isopropylmalate isomerase activity.

In embodiments, microbial organisms including at least one genetically modified LeuCD' enzyme complexes are disclosed. The LeuCD' enzyme complex includes (a) a genetically modified LeuC' subunit including: (1) an amino acid sequence with at least 80% homology to SEQ ID NO: 1 having a C-terminus; and (2) a C-terminal amino acid or peptide coupled to the C-terminus of the amino acid sequence of (a)(1), wherein the C-terminal amino acid is chosen from any naturally occurring amino acid, and wherein the C-terminal peptide includes an amino acid sequence: $(Xaa)_1(Xaa)_2(Xaa)_3(Xaa)_4(Xaa)_5(Xaa)_6(Xaa)_7(Xaa)_8(Xaa)_9(Xaa)_{10}$ (SEQ ID NO: 39). $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ of SEQ ID NO: 39 are each independently chosen from any naturally occurring amino acid, or are absent, provided that at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in the C-terminal peptide. The LeuCD' enzyme complex also includes (b) a LeuD subunit including an amino acid sequence with at least 80% homology to SEQ ID NO: 2, wherein the genetically modified LeuCD' enzyme complex has isopropylmalate isomerase activity.

In embodiments, processes for preparing $C_7$-$C_{11}$ 2-ketoacids are disclosed. The processes include: (I) providing at least one of a $C_4$-$C_{10}$ 2-ketoacid substrate with: (A) at least one isopropylmalate synthase enzyme having isopropylmalate synthase activity; (B) at least one isopropylmalate dehydrogenase enzyme having isopropylmalate dehydrogenase activity; and (C) at least one genetically modified LeuCD' enzyme complex. The genetically modified LeuCD' enzyme complex includes (1) a genetically modified LeuC' subunit including: (i) an amino acid sequence with at least 80% homology to SEQ ID NO: 1 having a C-terminus; and (ii) a C-terminal amino acid or peptide coupled to the C-terminus of the amino acid sequence of (I)(C)(1)(i), wherein the C-terminal amino acid is chosen from any naturally occurring amino acid, and wherein the C-terminal peptide includes an amino acid sequence: $(Xaa)_1(Xaa)_2(Xaa)_3(Xaa)_4(Xaa)_5(Xaa)_6(Xaa)_7(Xaa)_8(Xaa)_9(Xaa)_{10}$ (SEQ ID NO: 39). $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ of SEQ ID NO: 39 are each independently chosen from any naturally occurring amino acid, or are absent, provided that at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in the C-terminal peptide. The genetically modified LeuCD' enzyme complex also includes (2) a LeuD subunit including an amino acid sequence with at least 80% homology to SEQ ID NO: 2. The $C_4$-$C_{10}$ 2-ketoacid substrate is provided under conditions that the at least one of the $C_4$-$C_{10}$ 2-ketoacid substrate is converted to the $C_7$-$C_{11}$ 2-ketoacid. The genetically modified LeuCD' enzyme complex has isopropylmalate isomerase activity, and conversion of the at least one of the $C_4$-$C_{10}$ 2-ketoacid substrate to the $C_7$-$C_{11}$ 2-ketoacid occurs via one or more biochemical reactions.

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

BRIEF DESCRIPTION OF THE DRAWINGS

FIG. 1 shows the elongation of a 2-ketoacid by the recursive activities of isopropylmalate synthase (LeuA in *E. coli*), isopropylmalate isomerase (LeuCD in *E. coli*), isopropylmalate dehydrogenase (LeuB in *E. coli*) (collectively termed "the LeuABCD pathway" in *E. coli*), as depicted in (1) to (3). Following elongation, the resulting elongated 2-ketoacid (IV) is converted to an aldehyde (V) via the activity of a (thiamin dependent) decarboxylase in (4), and finally to an alcohol (VI) via the activity of an alcohol dehydrogenase in (5);

FIG. 2 shows two related but different routes to produce 1-heptanol. In the first route, a Wood-Ljungdahl pathway converts synthesis gas to acetyl CoA, and another pathway then converts the acetyl CoA to pyruvate. The pyruvate is then converted to 2-ketobutyrate, and finally a LeuABCD pathway is initiated, wherein the 2-ketobutyrate is converted to $C_7$-$C_{11}$ 2-ketoacid (in this embodiment, 2-keto-octanoate). Once the elongated 2-ketoacid has been formed (in this embodiment, the 2-keto-octanoate), a (thiamin dependent) decarboxylase (i.e., DC) converts it to a $C_6$-$C_{10}$ aldehyde, and an alcohol dehydrogenase (i.e., ADH) converts the $C_6$-$C_{10}$ aldehyde to a $C_6$-$C_{10}$ alcohol (in this embodiment, 1-heptanol). In the second route, one of the potential sugar catabolism pathways, which in this embodiment is a glycolysis or pentose phosphate pathway, converts a $C_5$ or $C_6$ sugar to pyruvate, and thereafter the same pathway sequence is followed as in the first route to reach the heptanol;

FIG. 3 shows a model of the LeuCD active site, which is formed at the interface of the LeuC subunit and the LeuD subunit. The model was created using homology modeling and using the crystal structures of pig aconitase (PDB ID code 1ACO) and isopropylmalate isomerase small subunit of *Campylobacter jejuni* (PDB ID code 3Q3W) as templates. The active site is modeled with the 2-hexylmalate (i.e., 2-HM) and the 4Fe-4S cluster. Various combinations of the residues Val-35 and Leu-411 in the LeuC subunit, and Leu-31 and His-88 in the LeuD subunit were modified in the instantly disclosed genetically modified LeuCD' enzyme complexes;

FIG. 4. Highly conserved amino acid residues in the large subunit of isopropylmalate isomerase. Shown are the highly conserved amino acid residues identified following an alignment of non-redundant protein sequences of the large subunit of isopropylmalate isomerase that diverged from the *E. coli* LeuC sequence by as much as 1-60%. Amino acid residues that were highly conserved across the protein sequences are shaded and are believed to play an important role in the functioning of the LeuC during the elongation of 2-ketoacids. Amino acid residues that are boxed are believed to form the active site of isopropylmalate isomerase;

FIG. 5. Highly conserved amino acid residues in the small subunit of isopropylmalate isomerase. Shown are the highly conserved amino acid residues identified following an alignment of non-redundant protein sequences of the small subunit of isopropylmalate isomerase that diverged from the *E. coli* LeuD sequence by as much as 1-60%. Amino acid residues that were highly conserved across the protein sequences are shaded and are believed to play an important role in the functioning of the LeuD during the elongation of 2-ketoacids. Amino acid residues that are boxed are believed to form the active site of isopropylmalate isomerase;

FIG. 8A shows the LeuD variant gene cassette, while FIG. 8B shows the LeuC variant gene cassette;

FIG. 9 (top graph) shows ANOVA analyses and Student's t-tests performed using SAS JMP 11.2.0 using a 90% confidence interval for the heptanol titers generated by +1 Pathway *E. coli* strains containing the WT and variant LeuC and LeuD enzymes. FIG. 9 (bottom graph) shows ANOVA analyses and Student's t-tests performed using SAS JMP 11.2.0 using a 90% confidence interval for the octanol titers generated by +1 Pathway *E. coli* strains containing the WT and variant LeuC and LeuD enzymes;

FIG. 10A shows a bar graph of a variant LeuCD enzyme having a LeuC subunit with an N-terminus $(His)_6$-tag (i.e., WT leuC (N-His)) and a variant of LeuCD enzyme having a LeuC subunit with a C-terminus $(His)_6$-tag (i.e., WT leuC (C-His)) with respect to moles of 3-isopropylmalate (which is produced via isomerization of 2-isopropylmalate by LeuCD) converted to 2-ketoisocaproate by LeuB per unit time (i.e., 2-ketoisocaproate (nmol/hr));

FIG. 10B is a bar graph of a variant LeuCD enzyme having a LeuC subunit with an N-terminus $(His)_6$-tag (i.e., WT leuC (N-His)) and a variant of LeuCD enzyme having a LeuC subunit with a C-terminus $(His)_6$-tag (i.e., WT leuC (C-His)) with respect to moles of 3-hexylmalate (which is produced via isomerization of 2-hexylmalate by LeuCD) converted to 2-ketononanoate by LeuB per unit time (i.e., 2-ketononanoate (nmol/hr)).

DETAILED DESCRIPTION

Figure 1:
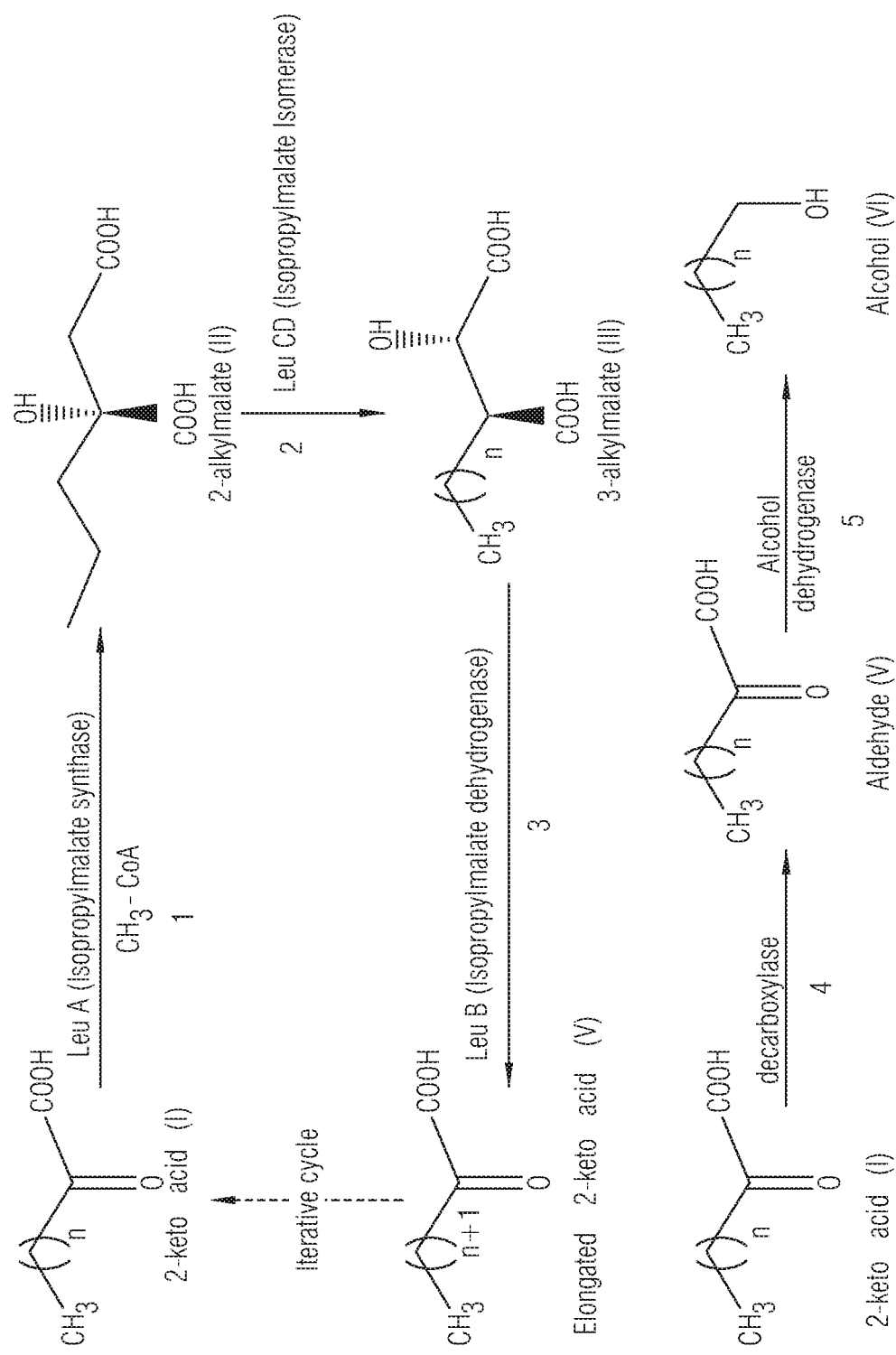
FIG. 1. Elongation of a 2-ketoacid.

While the following terms are believed to be well understood by one of ordinary skill in the art, definitions are set forth to facilitate explanation of presently-described subject matter.

As used herein, the singular forms "a," "an" and "the" include plural referents unless the context clearly dictates otherwise. Thus, for example, reference to "a" component includes aspects having two or more such components, unless the context clearly indicates otherwise.

As used herein and depending on the context, the terms "genetically modified" and "modified," refer to isopropylmalate isomerase enzyme complexes, such as, e.g., LeuCD, having intentionally altered amino acid sequences, i.e., non-wild type amino acid sequences. Depending on the context, genetically modified and modified may also refer to microbial organisms having a genome that has been intentionally altered as to include genetically modified isopropylmalate isomerase enzyme complexes, such as, e.g., genetically modified LeuCD'.

As used herein, the term "amino acid" refers to naturally occurring L α-amino acids or residues. The commonly used one- and three-letter abbreviations for naturally occurring amino acids or residues are used herein. Amino acid also includes D-amino acids or residues as well as naturally occurring amino acids or residues that are not usually incorporated into proteins or peptides, such as, e.g., norleucine.

As used herein, the terms "homology" and "homologous" refer to amino acid sequences of two proteins (or a region thereof) having a certain percentage identity, e.g., at least about 80%, 85%, 90%, 91%, 92%, 93%, 94%, 95%, 96%, 97%, 98%, or 99% identity. Percentage homology can be determined as is known to one of ordinary skill in the art. For example, to determine the percentage identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). As is known in the art, the percentage identity between two sequences is a function of the number of identical positions shared by the sequences, taking into account the number of gaps, and the length of each gap, which need to be introduced for optimal alignment of the two sequences. Sequence homology for polypeptides is typically measured using sequence analysis software.

When homologous is used in reference to proteins or peptides, it is recognized that amino acid residue positions that are not identical can often differ by conservative amino acid substitutions. For example, amino acid sequences having the function of LeuC or LeuD can be identified by performing a protein-protein BLAST (i.e., blastp) search of the non-redundant protein sequences (i.e., nr) database using the amino acid sequences of these proteins as query. The search can be conducted on the National Center for Biotechnology Information (i.e., NCBI) website (http://blast.ncbi.nlm.nih.gov) using default parameters.

As used herein, the terms, "peptide" and "peptides" refer to a molecule having at least two amino acids and up to thirty amino acids. In embodiments, the peptide includes a molecule having a chain of from at least two consecutive amino acids to thirty consecutive amino acids coupled via peptide bonds (i.e., an amino acid sequence of at least two amino acids to thirty amino acids). In embodiments, the peptides described herein include a chain of from two to thirty consecutive amino acids, or a chain of from four to twenty consecutive amino acids, or a chain of from six to fifteen consecutive amino acids, or a chain of from eight to ten consecutive amino acids, or a chain of ten consecutive amino acids.

As used herein, the terms "substrate" and "suitable substrate" refer to any substance or compound that is converted or meant to be converted into another compound by the action of an enzyme. The terms include not only a single compound, but also combinations of compounds, such as, e.g., solutions, mixtures and other materials which contain at least one substrate, or derivative thereof. Further, substrate and suitable substrate may encompass not only compounds that provide a carbon source suitable for use as a starting material, such as, e.g., any biomass derived sugar, but also intermediate and end product metabolites used in a pathway associated with a microbial organism as described herein.

Reference will now be made in detail to various embodiments of genetically modified isopropylmalate isomerase enzyme complexes, such as, e.g., LeuCD' enzyme complexes, microbial organisms including genetically modified isopropylmalate isomerase enzyme complexes, and processes for preparing $C_7$-$C_{11}$ 2-ketoacids with genetically modified isopropylmalate isomerase enzyme complexes. The genetically modified isopropylmalate isomerase enzyme complexes, microbial organisms including genetically modified isopropylmalate isomerase enzyme complexes, and processes for preparing $C_7$-$C_{11}$ 2-ketoacids can be used to produce bio-based chemicals and industrial products as alternatives to using fossil fuels. The instantly-disclosed genetically modified isopropylmalate isomerase enzyme complexes, microbial organisms including genetically modified isopropylmalate isomerase enzyme complexes, and processes for preparing $C_7$-$C_{11}$ 2-ketoacids can be used for producing longer chain alkanes, alcohols, and carboxylic acids, both in vivo and in vitro.

Embodiments of genetically modified isopropylmalate isomerase enzyme complexes will now be described in detail. Thereafter, microbial organisms including genetically modified isopropylmalate isomerase enzyme complexes will be described. Then, embodiments of processes for preparing $C_7$-$C_{11}$ 2-ketoacids with genetically modified isopropylmalate isomerase enzyme complexes will be described.

I. Genetically Modified Isopropylmalate Isomerase Enzyme Complexes

In embodiments, genetically modified isopropylmalate isomerase enzyme complexes with isopropylmalate isomerase activity are disclosed. Isopropylmalate isomerase enzyme complexes are heterodimers including two subunits: a large subunit (e.g., LeuC in *E. coli*, SEQ ID NO: 1; GenBank: Accession No. NC 000913.3 Gene ID: 945076) and a small subunit (e.g., LeuD in *E. coli*, SEQ ID NO: 2; GenBank: Accession No. NC 000913.3 Gene ID: 945642). Isopropylmalate isomerase enzyme complexes are known to be endogenously expressed in *E. coli*, *Shigella*, such as, e.g., *Shigella flexneri* (GenBank: Accession No. WP_025757828), Enterobacteriaceae (GenBank: Accession No. WP_001140654), *Klebsiella pneumoniae* (GenBank: Accession No. WP_087787525), and *Citrobacter freundii* (GenBank: Accession No. WP_086538719). Additional amino acid sequences having the function of LeuC or LeuD can be identified by performing a protein-protein BLAST (i.e., blastp) search of the non-redundant protein sequences database using the amino acid sequences of these proteins as query. In embodiments, genetically modified isopropylmalate isomerase enzyme complexes (such as, e.g., genetically modified LeuCD' enzyme complexes) are included in cellular extracts from cells overexpressing the genetically modified isopropylmalate isomerase enzyme complexes.

In embodiments, genetically modified isopropylmalate isomerase enzyme complexes include: (a) a genetically modified large subunit, and (b) a small subunit, which when complexed, confer isopropylmalate isomerase activity. In embodiments, the genetically modified large subunit includes: (1) an amino acid sequence of the large subunit having a C-terminus, and (2) a C-terminal amino acid or peptide coupled to the C-terminus of the amino acid sequence of the large subunit. The amino acid sequence of the large subunit may be any wild type or genetically modified amino acid sequence known to one of ordinary skill in the art as conferring isopropylmalate isomerase activity when complexed with the small subunit of the genetically modified isopropylmalate isomerase.

In embodiments, the genetically modified large subunit is a genetically modified LeuC' subunit. In embodiments, the genetically modified LeuC' subunit includes a wild type amino acid sequence of LeuC having a C-terminus or a genetically modified amino acid sequence of LeuC having a C-terminus. The wild type amino acid sequence of LeuC is SEQ ID NO: 1. In SEQ ID NO: 1, the C-terminus is the amino acid at position 466, i.e., Lysine. In some embodiments, the genetically modified LeuC' subunit includes an amino acid sequence with at least 80% homology to SEQ ID NO: 1. In some embodiments, the genetically modified LeuC' subunit includes an amino acid sequence with at least 85%, 90%, 91%, 92%, 93%, 94%, 95%, 96%, 97%, 98%, or 99% homology to SEQ ID NO: 1.

In some embodiments, the genetically modified LeuC' subunit includes an amino acid sequence with at least 80% homology to SEQ ID NO: 1 which includes at least one specifically contemplated amino acid substitution. In further embodiments, the genetically modified LeuC' subunit includes an amino acid sequence with at least 80% homology to SEQ ID NO: 1, wherein alanine or glycine is substituted for Val-35 and/or wherein valine, alanine, or glycine is substituted for Leu-411. In illustrative, non-limiting embodiments, the genetically modified LeuC' subunit includes an amino acid sequence with at least 80% homology to SEQ ID NO: 1 and at least one amino acid substitution chosen from: (i) alanine for Val-35; (ii) glycine for Val-35; (iii) alanine for Val-35 and valine for Leu-411; (iv) alanine for Val-35 and alanine for Leu-411; (v) alanine for Val-35 and glycine for Leu-411; and (vi) glycine for Val-35 and valine for Leu-411.

In embodiments, the genetically modified large subunit includes a C-terminal amino acid or peptide coupled to the C-terminus of the amino acid sequence thereof. In some embodiments, the genetically modified large subunit includes a C-terminal amino acid, e.g., a single C-terminal amino acid, coupled to the C-terminus of the amino acid sequence thereof. In some embodiments, the genetically modified large subunit includes a C-terminal amino acid coupled to the C-terminus of the amino acid sequence of the genetically modified LeuC' subunit, as previously described herein. In some embodiments, the C-terminal amino acid is chosen from any naturally occurring amino acid. In some embodiments, the C-terminal amino acid consists essentially of or consists of a single amino acid.

In some embodiments, the genetically modified large subunit includes a C-terminal peptide. In some embodiments, the genetically modified large subunit includes a C-terminal peptide coupled to the C-terminus of the amino acid sequence of the genetically modified LeuC' subunit, as previously described herein. In embodiments, the C-terminal peptide has an amino acid sequence:

$$(Xaa)_1(Xaa)_2(Xaa)_3(Xaa)_4(Xaa)_5(Xaa)_6(Xaa)_7(Xaa)_8 \quad \text{(SEQ ID NO: 38)}$$
$$(Xaa)_9(Xaa)_{10}(Xaa)_{11}(Xaa)_{12}(Xaa)_{13}(Xaa)_{14}(Xaa)_{15}$$
$$(Xaa)_{16}(Xaa)_{17}(Xaa)_{18}(Xaa)_{19}(Xaa)_{20}(Xaa)_{21}(Xaa)_{22}$$
$$(Xaa)_{23}(Xaa)_{24}(Xaa)_{25}(Xaa)_{26}(Xaa)_{27}(Xaa)_{28}(Xaa)_{29}$$
$$(Xaa)_{30}$$

in which $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, $(Xaa)_{10}$, $(Xaa)_{11}$, $(Xaa)_{12}$, $(Xaa)_{13}$, $(Xaa)_{14}$, $(Xaa)_{15}$, $(Xaa)_{16}$, $(Xaa)_{17}$, $(Xaa)_{18}$, $(Xaa)_{19}$, $(Xaa)_{20}$, $(Xaa)_{21}$, $(Xaa)_{22}$, $(Xaa)_{23}$, $(Xaa)_{24}$, $(Xaa)_{25}$, $(Xaa)_{26}$, $(Xaa)_{27}$, $(Xaa)_{28}$, $(Xaa)_{29}$, and $(Xaa)_{30}$ are each independently chosen from any naturally occurring amino acid, or are absent. In some embodiments, each of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, $(Xaa)_{10}$, $(Xaa)_{11}$, $(Xaa)_{12}$, $(Xaa)_{13}$, $(Xaa)_{14}$, $(Xaa)_{15}$, $(Xaa)_{16}$, $(Xaa)_{17}$, $(Xaa)_{18}$, $(Xaa)_{19}$, $(Xaa)_{20}$, $(Xaa)_{21}$, $(Xaa)_{22}$, $(Xaa)_{23}$, $(Xaa)_{24}$, $(Xaa)_{25}$, $(Xaa)_{26}$, $(Xaa)_{27}$, $(Xaa)_{28}$, $(Xaa)_{29}$, and $(Xaa)_{30}$ is independently chosen from Ala, Arg, Asn, Asp, Cys, Gln, Glu, Gly, His, Ile, Leu, Lys, Met, Phe, Pro, Ser, Thr, Trp, Tyr, and Val, or is absent. In embodiments, at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, $(Xaa)_{10}$, $(Xaa)_{11}$, $(Xaa)_{12}$, $(Xaa)_{13}$, $(Xaa)_{14}$, $(Xaa)_{15}$, $(Xaa)_{16}$, $(Xaa)_{17}$, $(Xaa)_{18}$, $(Xaa)_{19}$, $(Xaa)_{20}$, $(Xaa)_{21}$, $(Xaa)_{22}$, $(Xaa)_{23}$, $(Xaa)_{24}$, $(Xaa)_{25}$, $(Xaa)_{26}$, $(Xaa)_{27}$, $(Xaa)_{28}$, $(Xaa)_{29}$, or $(Xaa)_{30}$ are present.

In embodiments, the C-terminal peptide has an amino acid sequence:

$$(Xaa)_1(Xaa)_2(Xaa)_3(Xaa)_4(Xaa)_5(Xaa)_6(Xaa)_7(Xaa)_8 \quad \text{(SEQ ID NO: 39)}$$
$$(Xaa)_9(Xaa)_{10}$$

in which $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ are each independently chosen from any naturally occurring amino acid, or are absent. In some embodiments, each of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ is independently chosen from Ala, Arg, Asn, Asp, Cys, Gln, Glu, Gly, His, Ile, Leu, Lys, Met, Phe, Pro, Ser, Thr, Trp, Tyr, and Val, or are absent. In some embodiments, if present, each of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ is independently chosen from hydrophobic, neutral hydrophilic, polar, acidic, charged, basic, chain orientation influencing, and aromatic naturally occurring amino acids. Hydrophobic naturally occurring amino acids may include His, Trp, Tyr, Phe, Met, Leu, Ile, Val, and Ala. Neutral hydrophilic naturally occurring amino acids may include Cys, Ser, and Thr. Polar naturally occurring amino acids may include Ser, Thr, Asn, and Gln. Acidic naturally occurring amino acids may include Asp and Glu. Charged naturally occurring amino acids may include: Asp and Glu (negatively charged); and Arg, Lys, and His (positively charged). Basic naturally occurring amino acids may include His, Lys, and Arg. Chain orientation influencing naturally occurring amino acids may include Gly and Pro. Aromatic naturally occurring amino acids may include Trp, Tyr, Phe, and His.

In some embodiments, if present, each of $(Xaa)_1$, $(Xaa)_2$, $(Xaa)_9$, and $(Xaa)_{10}$ is independently chosen from neutral hydrophilic and polar naturally occurring amino acids. In some embodiments, if present, each of $(Xaa)_1$, $(Xaa)_2$, $(Xaa)_9$, and $(Xaa)_{10}$ is independently chosen from Ser, Cys, Thr, Asn, and Gln. In further embodiments, if present, each of $(Xaa)_1$, $(Xaa)_2$, $(Xaa)_9$, and $(Xaa)_{10}$ is independently chosen from Ser and Thr. In yet further embodiments, if present, each of $(Xaa)_1$, $(Xaa)_2$, $(Xaa)_9$, and $(Xaa)_{10}$ is Ser.

In some embodiments, if present, each of $(Xaa)_3$, $(Xaa)_4$, $(Xaa)_5$, $(Xaa)_6$, $(Xaa)_7$, and $(Xaa)_8$ is chosen from hydrophobic, positively charged, basic, and aromatic naturally occurring amino acids. In some embodiments, if present, each of $(Xaa)_3$, $(Xaa)_4$, $(Xaa)_5$, $(Xaa)_6$, $(Xaa)_7$, and $(Xaa)_8$ is independently chosen from His, Trp, Tyr, Phe, Met, Leu, Ile, Val, Ala, Arg, and Lys. In further embodiments, if present, each of $(Xaa)_3$, $(Xaa)_4$, $(Xaa)_5$, $(Xaa)_6$, $(Xaa)_7$, and $(Xaa)_8$ is independently chosen from His, Lys, and Arg. In yet further embodiments, if present, each of $(Xaa)_3$, $(Xaa)_4$, $(Xaa)_5$, $(Xaa)_6$, $(Xaa)_7$, and $(Xaa)_8$ is His.

In some embodiments, each of $(Xaa)_3$, $(Xaa)_4$, $(Xaa)_5$, $(Xaa)_6$, $(Xaa)_7$, and $(Xaa)_8$ is His and each of $(Xaa)_1$, $(Xaa)_2$, $(Xaa)_3$, and $(Xaa)_4$ is absent from SEQ ID NO: 39; in these embodiments, the amino acid sequence SEQ ID NO: 39 is HisHisHisHisHisHis or (His)$_6$. In some embodiments, at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in SEQ ID NO: 39. In still further embodiments, at least four of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in SEQ ID NO: 39. In yet still further embodiments, at least six of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in SEQ ID NO: 39. In further embodiments, all of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ are present in SEQ ID NO: 39.

In illustrative, non-limiting embodiments, $(Xaa)_1$, $(Xaa)_2$, $(Xaa)_3$, and $(Xaa)_4$ are each Ser (and are all present), and $(Xaa)_3$, $(Xaa)_4$, $(Xaa)_5$, $(Xaa)_6$, $(Xaa)_7$, and $(Xaa)_8$ are each His (and are all present); in this illustrative embodiment, SEQ ID NO: 39 is SerSerHisHisHisHisHisHisSerSer (SEQ ID NO: 40). In other illustrative, non-limiting embodiments, the C-terminal peptide SEQ ID NO: 40 is linked to the C-terminus of the amino acid sequence of the wild type LeuC subunit, providing the amino acid sequence SEQ ID NO: 41.

In embodiments, the C-terminal amino acid or peptide is coupled via a peptide bond to the C-terminus of the large subunit. In some embodiments, the C-terminal amino acid or peptide is coupled via a peptide bond to the C-terminus of the genetically modified LeuC' subunit, as previously described herein. In illustrative, non-limiting embodiments, the N-terminus of the C-terminal peptide is coupled via a peptide bond to the large subunit, e.g., the genetically modified LeuC' subunit. In SEQ ID NO: 38, the N-terminus is $(Xaa)_1$, if present, and the C-terminus is $(Xaa)_{30}$, if present. In SEQ ID NO: 39, the N-terminus is $(Xaa)_1$, if present, and the C-terminus is $(Xaa)_{10}$, if present.

In some embodiments, the C-terminal peptide includes an amino acid chain of from two to thirty consecutive amino acids in length, or an amino acid chain of from four to twenty consecutive amino acids in length, or an amino acid chain of from six to fifteen consecutive amino acids in length, or an amino acid chain of from eight to ten consecutive amino acids in length, or an amino acid chain of ten consecutive amino acids in length. In some embodiments, the C-terminal peptide includes an amino acid chain of from six to ten consecutive amino acids in length. In some embodiments, the C-terminal peptide of the large subunit consists essentially of or consists of SEQ ID NO: 38 or SEQ ID NO: 39. In some embodiments, the C-terminal peptide of the large subunit consists essentially of or consists of SEQ ID NO: 40.

In embodiments, genetically modified isopropylmalate isomerase enzyme complexes include a small subunit, which when complexed with the large subunit, confer isopropylmalate isomerase activity. In embodiments, the genetically modified small subunit includes any wild type or genetically modified amino acid sequence known to one of ordinary skill in the art as conferring isopropylmalate isomerase activity when complexed with the large subunit of the genetically modified isopropylmalate isomerase. In some embodiments, the small subunit is a LeuD subunit. In embodiments, the LeuD subunit includes a wild type amino acid sequence of LeuD or a genetically modified amino acid sequence of LeuD. The wild type amino acid sequence of LeuD is SEQ ID NO: 2. In some embodiments, the LeuD subunit includes an amino acid sequence with at least 80% homology to SEQ ID NO: 2. In some embodiments, the LeuD subunit includes an amino acid sequence with at least 85%, 90%, 91%, 92%, 93%, 94%, 95%, 96%, 97%, 98%, or 99% homology to SEQ ID NO: 2.

In some embodiments, the LeuD subunit includes an amino acid sequence with at least 80% homology to SEQ ID NO: 2 which includes at least one specifically contemplated amino acid substitution. In further embodiments, the LeuD subunit includes an amino acid sequence with at least 80% homology to SEQ ID NO: 2 wherein alanine, glycine, valine, or serine is independently substituted for Leu-31 and/or His-88. In illustrative, non-limiting embodiments the LeuD subunit includes an amino acid sequence with at least 80% homology to SEQ ID NO: 2 with at least one amino acid substitution chosen from: (i) alanine for Leu-31; (ii) glycine for Leu-31; (iii) valine for Leu-31; (iv) alanine for Leu-31 and serine for His-88; (v) glycine for Leu-31 and alanine for His-88; (vi) glycine for Leu-31 and serine for His-88; and (vii) valine for Leu-31 and alanine for His-88.

In embodiments wherein the large subunit is genetically modified LeuC' and the small subunit is LeuD, the genetically modified isopropylmalate isomerase enzyme complex is a genetically modified LeuCD' enzyme complex. In some embodiments, the genetically modified LeuCD' enzyme complex includes amino acid substitutions altering the wild type amino acid sequences of LeuC and LeuD. In some embodiments, the amino acid substitutions previously described herein of LeuC and LeuD have been identified as exhibiting improved activity and catalytic efficiency (i.e., $k_{cat}/K_m$) at isomerizing longer chain 2-alkylmalates, such as e.g., $C_4$-$C_6$ 2-alkylmalates, to their corresponding 3-alkylmalates in comparison with the wild type E. coli LeuCD enzyme complex (LeuC: EcoGene Accession Number EG11576, Gene ID 945076; and LeuD: EcoGene Accession Number EB11575, Gene ID: 945642). Various sites (i.e., positions) within the wild type LeuC sequence (SEQ ID NO: 1) and wild type LeuD sequence (SEQ ID NO: 2) have been identified as key to obtaining the improvements. The key sites identified within the wild type sequence of LeuC include Val-35, Leu-411, and combinations thereof. The key sites identified within the wild type sequence of LeuD include Leu-31, His-88, and combinations thereof. In LeuC, alterations may be made wherein: alanine or glycine is substituted for Val-35 and/or wherein valine, alanine, or glycine is substituted for Leu-411. In LeuD, alternations may be made wherein valine, alanine, or glycine is substituted for Leu-31 and/or wherein serine or alanine is substituted for His-88. The substitutions can vary from single-site (i.e. single amino acid constituting three base pairs) substitution in either LeuC or LeuD, to multiple-site (e.g., from 2-4 sites) substitutions within both LeuC and LeuD. SEQ ID NOs: 3-37 are amino acid sequences of LeuC and LeuD variants including one or more of these substitutions.

Referencing FIG. 4, an alignment of amino acid sequences of the large subunit of isopropylmalate isomerase enzyme complexes that diverged from the E. coli LeuC amino acid sequence by as much as 60%, demonstrated that more than 80% of aligned sequences shared the 284 shaded amino acid residues in FIG. 4. Based on this alignment, amino acids that are shaded in FIG. 4 may be considered to be necessary for conferring LeuC function (such as, e.g., folding, substrate binding, specificity, catalysis etc.) in the same way as in E. coli LeuC. Additionally, and without being bound by the theory, it is believed that the active site of LeuCD includes the following amino acids of LeuC: V32-S37, D62-N64, G106-V110, G127-T131, C220-M222, G345-T348, G406-A412, S428-N431, and G434-Q436 (shown as boxed in FIG. 4).

Similarly, referencing FIG. 5, an alignment of amino acid sequences of the small subunit of isopropylmalate isomerase enzyme complexes that diverged from the E. coli LeuD amino acid sequence by as much as 60%, demonstrated that more than 80% of aligned sequences shared the 101 shaded amino acids with the E. coli LeuD amino acid sequence. Based on this alignment, amino acids that are shaded in FIG. 5 may be considered to be necessary for conferring LeuD function (such as, e.g., folding, substrate binding, specificity, catalysis etc.) in the same way as in E. coli LeuD. Additionally, and without being bound by the theory, it is believed that the active site of LeuCD includes the following amino acids of LeuD: T22-D23, P27-L31, and G83-E87 (shown as the boxed regions in FIG. 5).

In embodiments, amino acids which are not believed to be necessary for the functioning of isopropylmalate isomerase enzyme complexes (e.g., amino acid residues that are not shaded in FIG. 4 for LeuC, and amino acid residues that are not shaded in FIG. 5 for LeuD) may be substituted conservatively or non-conservatively, and it is believed that such amino acid substitutions would not significantly diminish the functional properties of the modified isopropylmalate isomerase enzyme complexes as compared to wild type E. Coli LeuCD. In embodiments, amino acids which are not believed to form the active site of isopropylmalate isomerase but are still considered necessary for the functioning of isopropylmalate isomerase enzyme complexes (e.g., amino acid residues that are shaded but not boxed in FIG. 4 for LeuC and amino acid residues that are shaded but not boxed in FIG. 5 for Leu 5) may be conservatively substituted, and it is believed that such amino acid substitutions would not significantly diminish the functional properties of the genetically modified isopropylmalate isomerase enzyme complexes as compared to wild type E. coli LeuCD. In embodiments, it is believed that most conservative and nonconservative amino acid substitutions for amino acids which are believed to form the active site of isopropylmalate isomerase enzyme complexes (e.g., amino acid residues that are shaded and boxed in FIG. 4 for LeuC and amino acid residues that are shaded and boxed in FIG. 5 for LeuD), other than those specific amino acid substitutions described previously herein, would diminish the functional properties of the genetically modified isopropylmalate isomerase enzyme complexes as compared to wild type E. coli LeuCD. It is believed that genetically modified large and/or small subunits of isopropylmalate isomerase enzyme complexes (e.g., LeuCD') having the contemplated substitutions would confer isopropylmalate isomerase activity. Stated another way, it is believed that the amino acid substitutions contemplated herein would not significantly diminish the functional properties of the modified isopropylmalate isomerase enzyme complexes as compared to wild type E. Coli LeuCD.

The genetically modified isopropylmalate isomerase enzyme complexes described herein (including genetically modified LeuCD' enzyme complexes) may be produced via any methods known to one of ordinary skill in the art. For example, the genetically modified isopropylmalate isomerase enzyme complexes may be produced via chemical synthesis and/or recombinant technology. Recombinant technology may include: inserting a gene (either natural or synthetic) which encodes the protein or peptide of interest (e.g., the genetically modified isopropylmalate isomerase enzyme complex, a subunit thereof, and/or the C-terminal peptide described previously herein) into an appropriate vector; inserting the vector into an appropriate host cell (such as, e.g., a target microbial organism); culturing the host cell to cause expression of the gene; and recovering or isolating the protein or peptide of interest expressed in the host cell.

The genetically modified isopropylmalate isomerase enzyme complexes described herein (including genetically modified LeuCD' enzyme complexes) may also be modified to include the amino acid substitutions contemplated herein via site-directed mutagenesis, as is known to one of ordinary skill in the art. Site-directed mutagenesis will result in the conversion of at least one nucleic acid to a different nucleic acid, which can effect an amino acid substitution. Combinations of any of the production methods described herein may also be employed.

Embodiments of genetically modified isopropylmalate isomerase enzyme complexes have been described in detail. Microbial organisms including genetically modified isopropylmalate isomerase enzyme complexes will now be described. Thereafter, embodiments of processes for preparing $C_7$-$C_{11}$ 2-ketoacids with genetically modified isopropylmalate isomerase enzyme complexes will be described.

II. Microbial Organisms Including Genetically Modified Isopropylmalate Isomerase Enzyme Complexes In embodiments, microbial organisms including genetically modified isopropylmalate isomerase enzyme complexes are disclosed. The genetically modified isopropylmalate isomerase enzyme complexes are as previously described herein and have isopropylmalate isomerase activity. In some embodiments, the microbial organisms include at least one genetically modified LeuCD' enzyme complex. The LeuCD' enzyme complex is as previously described herein.

In embodiments, the genetically modified isopropylmalate isomerase enzyme complexes, e.g., genetically modified LeuCD' enzyme complexes, are expressed in the microbial organism and have isopropylmalate isomerase activity. In some embodiments, the microbial organism is one known or believed to possess one or more desired metabolic pathways and/or other features, such as, e.g., resistance to growth inhibition by a $C_6$-$C_{10}$ product, as described in greater detail subsequently herein. For example, the microbial organism may possess a native metabolic pathway capable of producing a suitable substrate (such as, e.g., 2-ketobutyrate, 2-ketoisovalerate, and/or 2-methyl-2-keto pentanoate), a native type "+1" pathway (or the LeuABCD pathway, as it is termed with respect to E. coli), and/or a native pathway capable of converting products of the "+1" pathway to $C_7$-$C_{11}$ 2-ketoacids, $C_6$-$C_{10}$ aldehydes, $C_6$-$C_{10}$ alcohols, $C_6$-$C_{10}$ carboxylic acids, and/or $C_5$-$C_9$ alkanes. These pathways will be described in detail subsequently herein.

With regard to microbial organisms possessing native metabolic pathways capable of producing a suitable substrate, the genetically modified isopropylmalate isomerase enzyme complex may be expressed in a microbial organism possessing a metabolic pathway capable of producing acetyl CoA. In embodiments, referencing FIG. 2, production of acetyl CoA may be via either an anabolic (e.g., Wood-Ljungdahl) or catabolic (e.g., glycolysis, or a pentose phosphate pathway) route. In some embodiments, the microbial organism possesses a Wood-Ljungdahl pathway, also known as a "synthesis gas (syngas) fixation pathway," wherein syngas is converted to acetyl CoA. Certain acetate-producing bacteria possess the Wood-Ljungdahl pathway. For example, bacteria of the genus Clostridium, including Clostridium ljungdahlii (i.e., C. ljungdahlii) possess the Wood-Ljungdahl pathway. In the Wood-Ljungdahl pathway, syngas may be converted to acetyl CoA via reduction of carbon dioxide to carbon monoxide and then to acetyl CoA. This may be accomplished via the action of two enzymes: carbon monoxide dehydrogenase and acetyl CoA synthase. Carbon monoxide dehydrogenase catalyzes reduction of carbon dioxide and acetyl CoA synthase combines the resulting carbon monoxide with a methyl group to form acetyl CoA. From this point, acetyl CoA can continue via additional pathways for conversion to pyruvate via reduction by ferrodoxin oxidoreductase (i.e., PFO).

Figure 2:
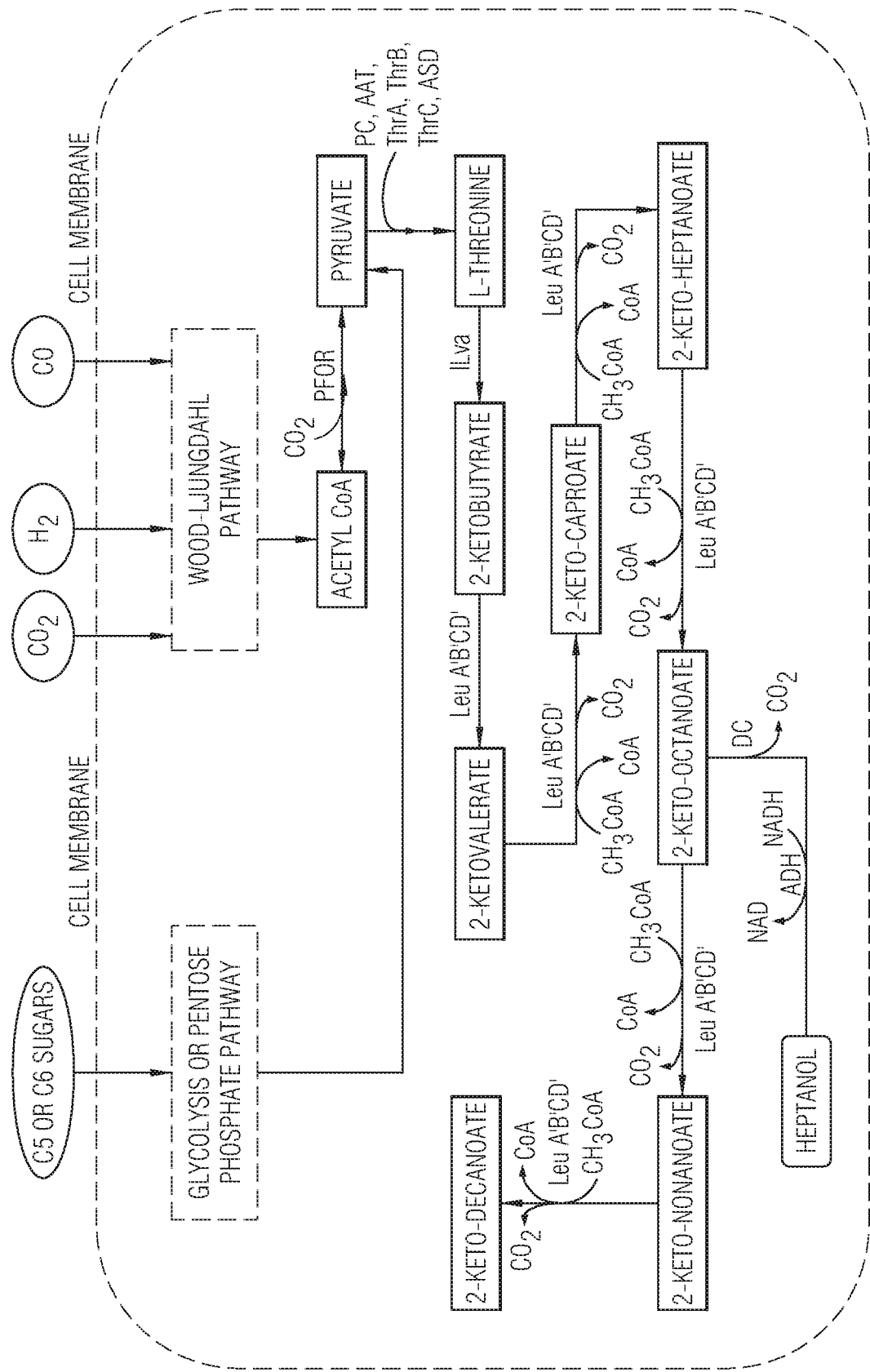
FIG. 2. Two pathways to produce 1-heptanol.

In some embodiments, still referencing FIG. 2, the microbial organism possesses a sugar catabolism pathway, such as, e.g., a glycolysis or pentose phosphate pathway. In these embodiments, the microbial organism converts a suitable (e.g., a non-syngas) carbon-containing substrate, such as e.g., a $C_5$ or $C_6$ sugar including glucose, sucrose, and/or pentose, directly to pyruvate via sugar catabolism. Such sugar catabolism pathways may be present in microbial organisms including, for example, Clostridium acetobutylicum, Escherichia coli (i.e., E. coli), Lactobacillus brevis, Pseudomonas putida, Bacillus subtilis, Saccharomyces cerevisiae, and Corynebacterium glutamicum.

Upon conversion of the syngas or non-syngas substrate to pyruvate (via either the Wood-Ljungdahl pathway or a sugar catabolism pathway), the pyruvate may be converted to L-threonine, via activity of pyruvate carboxylase (i.e., PC), aspartate aminotransferase (i.e., AAT), ThrABC (which includes ThrA (a bifunctional aspartokinase/homoserine dehydrogenase), ThrB (a homoserine kinase), and ThrC (a threonine synthase)), and aspartate semialdehyde dehydrogenase (i.e., ASD). L-threonine may then be converted to 2-ketobutyrate via threonine dehydratase (i.e., Ilva). In some embodiments, pyruvate is converted to 2-ketoisovalerate via activity of IlvBN/IlvGM, IlvC, and IlvD. In some embodiments, the pyruvate is converted to 2-methyl-2-keto pentanoate via a number of biochemical reactions.

Following production of 2-ketobutyrate, 2-ketoisovalerate, and/or 2-methyl-2-keto pentanoate, genetic modification of the native "+1" pathway portion (or the native LeuABCD portion in E. coli) of the leucine biosynthesis pathway effects conversion thereof to a $C_7$-$C_{11}$ 2-ketoacid via a number of biochemical reactions. The genetically modified "+1" pathway may employ at least one wild type or genetically modified enzyme thereof; however, in the context of this disclosure, the genetically modified "+1" pathway employs genetically modified isopropylmalate isomerase, e.g., LeuCD', as previously described herein. For example, the genetically modified "+1" pathway may include wild type (referred to as, LeuA, LeuB, LeuC, and/or LeuD) and/or genetically modified (referred to as LeuA', LeuB', LeuC', and/or LeuD') enzymes of the LeuABCD pathway.

In embodiments, referencing FIG. 1, the wild type and/or genetically modified enzymes of the LeuABCD pathway convert 2-ketobutyrate, 2-ketoisovalerate, and/or 2-methyl-2-keto pentanoate to a desired $C_7$-$C_{11}$ 2-ketoacid. For example, 2-ketobutyrate may be converted first to 2-ketovalerate, then to 2-ketocaproate, then to 2-ketoheptanoate or to 2-keto-undecanoate, i.e., a desired $C_7$-$C_{11}$ 2-ketoacid, as chain-lengthening occurs through the "+1" pathway. As another example, 2-ketoisovalerate may be converted first to 2-ketoisocaproate, then to 2-ketoisoheptanoate. Enzymes (wild-type or genetically modified) accomplishing chain elongation in the "+1" pathway may include isopropylmalate synthase having isopropylmalate synthase activity (e.g., LeuA and/or LeuA'), isopropylmalate dehydrogenase having isopropylmalate dehydrogenase activity (e.g., LeuB and/or LeuB'), and/or a genetically modified isopropylmalate isomerase having isopropylmalate isomerase activity (e.g., LeuCD'). In some embodiments, only one enzyme is genetically modified, e.g., genetically modified isopropylmalate isomerase. For example, the chain elongation enzymes may include only genetically modified LeuCD', while the remaining enzymes are wild type. The choice of enzymes is such that desirable production of a $C_7$-$C_{11}$ 2-ketoacid beginning with 2-ketobutyrate or 2-ketoisovalerate is achieved.

Further disclosure regarding modification of non-natural leucine biosynthesis pathways is described in co-pending International Publication No. WO/2015/089127, which is incorporated herein in its entirety by reference. In some embodiments, LeuA', LeuB', and/or LeuCD' (as previously described herein) are utilized, as described in International Publication No. WO/2015/089127. In some embodiments, a wild type LeuA, a genetically modified LeuA', a wild type LeuB, a genetically modified LeuB, and genetically modified LeuCD' are utilized in combination. With specific regard to LeuA, LeuA (GenBank Accession No. NC_000913.3 Gene ID: 947465) can be genetically modified to produce an isopropylmalate synthase variant (i.e., LeuA') having a higher-than-average catalytic efficiency ($k_{cat}/K_m$) for capturing 2-ketoacids of interest for catalysis.

Once an elongated $C_7$-$C_{11}$ 2-ketoacid is formed, the elongated $C_7$-$C_{11}$ 2-ketoacid may be used as is, or converted to a $C_6$-$C_{10}$ aldehyde. For conversion to a $C_6$-$C_{10}$ aldehyde, a wild type or genetically modified thiamin dependent decarboxylase is employed, resulting in a $C_6$-$C_{10}$ aldehyde having one less carbon atom than the $C_7$-$C_{11}$ 2-ketoacid being converted. $C_6$-$C_{10}$ aldehydes have wide applicability, such as, e.g., as starting substrates or intermediates in producing $C_6$-$C_{10}$ alcohols, $C_6$-$C_{10}$ carboxylic acids, $C_5$-$C_9$ alkanes, and combinations thereof, as described in greater detail subsequently herein.

In embodiments, the microbial organism is chosen from *Escherichia coli, Lactobacillus brevis, Pseudomonas putida*, a *Clostridium* species, e.g., *Clostridium ljungdahlii* or *Clostridium autoethanogenum*, a *Bacillus* species, e.g., *Bacillus subtilis*, a *Saccharomyces* species, e.g., *Saccharomyces cerevisiae*, and/or a *Corynebacterium* species, e.g., *Corynebacterium glutamicum*. In some embodiments, the microbial organism is chosen from *Escherichia coli, Lactobacillus brevis, Pseudomonas putida, Clostridium ljungdahlii, Clostridium autoethanogenum, Bacillus subtilis, Saccharomyces cerevisiae*, or *Corynebacterium glutamicum*. In some embodiments, the microbial organism is *Escherichia coli*. In embodiments, the microbial organisms described herein may be used for large or otherwise commercial scale fermentative production of an enzyme-facilitated product, such as a $C_6$-$C_{10}$ aldehydes and/or one of $C_6$-$C_{10}$ products prepared therefrom.

In embodiments, preparation of genetically modified microbial organisms may be carried out via recombinant technology, such as, e.g., inserting a gene encoding the genetically modified isopropylmalate isomerase enzyme complex of choice into an appropriate vector, and inserting the vector into an appropriate host cell such as, e.g., a target microbial organism. In general, the examples disclosed herein demonstrate recombinant engineering to alter one or more nucleic acid bases in a given codon in order to alter the amino acid encoded thereby. Such recombinant techniques may be used to produce genetically modified enzymes and/or microbial organisms for in vitro assay purposes. In contrast, in some embodiments, the genome of a microbial organism may be altered for larger scale production strains. These preparation methods may be carried out via any suitable methods known to one of ordinary skill in the art.

By way of example, a suitable database, such as GenBank, may be used to obtain genetic codes for target wild type enzymes, and suitable codons thereof may be identified. Codon identification may be used as the basis for methods of protein engineering known to one of ordinary skill in the art. Specifically contemplated amino acid substitutions in a target enzyme may be effected via site-directed mutagenesis of nucleic acids, as previously described herein, to obtain a resulting gene. The resulting gene may then be cloned into a vector, such as, e.g., a replicative plasmid vector, and the vector may be transformed into a host microbial organism. The vector should be capable of enabling expression of the target enzymes, which, in some instances, have a higher-than-wild type catalytic efficiency against natural or non-natural substrates. The target enzymes may then be isolated from the host microbial organism and used, with or without purification, to yield an enzyme containing solution. In some instances, the enzyme containing solution exhibits a higher than wild type catalytic efficiency against natural or non-natural substrates.

In some embodiments, it is possible to identify a microbial organism having wild type enzymes that are useful in a desired pathway, and either use that microbial organism as a host microbial organism or transfer a suitable enzyme-encoding portion of the genome thereof into the genome of a different host microbial organism. In some embodiments, the host microbial organism is an organism that has been identified as being useful for large scale fermentation production. By way of example, microbial organisms that produce a suitable wild type thiamin dependent decarboxylase (i.e., DC) and/or wild type alcohol dehydrogenase (i.e., ADH) could be selected, and that microbial organism could be used as a host microbial organism or as a transformant microbial organism to prepare a genetically modified microbial organism, as previously described herein.

Embodiments of microbial organisms including genetically modified isopropylmalate isomerase enzyme complexes have been described in detail. Now, embodiments of processes for preparing $C_7$-$C_{11}$ 2-ketoacids with genetically modified isopropylmalate isomerase enzyme complexes will be described.

III. Processes for Preparing $C_7$-$C_{11}$ 2-Ketoacids with Genetically Modified Genetically Modified Isopropylmalate Isomerase Enzyme Complexes In embodiments, processes for preparing $C_7$-$C_{11}$ 2-ketoacids are disclosed. In some embodiments, processes for preparing a $C_7$-$C_{11}$ 2-ketoacid include providing at least one of a $C_4$-$C_{10}$ 2-ketoacid substrate with a series of enzymes including a genetically modified isopropylmalate isomerase enzyme complex, e.g., a genetically modified LeuCD' enzyme complex. In some embodiments, processes for preparing $C_7$-$C_{11}$ 2-ketoacids include providing a starting substrate and a series of enzymes that act on the substrate or a product thereof. In some embodiments, the series of enzymes ultimately convert the substrate to a desired $C_7$-$C_{11}$ 2-ketoacid.

In some embodiments a process for preparing a $C_7$-$C_{11}$ 2-ketoacid includes: (I) providing at least one of a $C_4$-$C_{10}$ 2-ketoacid substrate with (A) at least one isopropylmalate synthase having isopropylmalate synthase activity, (B) at least one isopropylmalate dehydrogenase having isopropylmalate dehydrogenase activity, and (C) at least one genetically modified isopropylmalate isomerase enzyme complex having isopropylmalate isomerase activity, e.g., at least one genetically modified LeuCD' enzyme complex, under conditions that the at least one of the $C_4$-$C_{10}$ 2-ketoacid substrate is converted to the $C_7$-$C_{11}$ 2-ketoacid. In some embodiments, the process further includes a wild type LeuCD enzyme complex. In some embodiments, the conversion of the least one $C_4$-$C_{10}$ 2-ketoacid substrate to the $C_7$-$C_{11}$ 2-ketoacid occurs via one or more biochemical reactions. The biochemical reactions may independently occur within or outside of a genetically modified microbial organism, as previously described herein. In some embodiments, the $C_4$-$C_{10}$ 2-ketoacid substrate includes 2-ketobutyrate. In some embodiments, the $C_4$-$C_{10}$ 2-ketoacid substrate includes 2-ketoisovalerate. In some embodiments, the $C_4$-$C_{10}$ 2-ketoacid substrate includes 2-methyl-2-ketopentanoate.

In some embodiments, referencing FIG. 2, the processes for preparing the $C_7$-$C_{11}$ 2-ketoacids, $C_6$-$C_{10}$ aldehydes, $C_6$-$C_{10}$ alcohols, $C_6$-$C_{10}$ carboxylic acids, or $C_5$-$C_9$ alkanes include converting a selected carbon-containing substrate to pyruvate, and then converting the pyruvate to either 2-ketobutyrate or to 2-ketoisovalerate, via the action of one or more enzymes. More specifically, in some embodiments, the carbon-containing substrate is provided and/or contacted with one or more enzymes such that the carbon-containing substrate is converted to 2-ketobutyrate, 2-ketoisovalerate, or 2-methyl-2-ketopentanoate. The 2-ketobutyrate, 2-ketoisovalerate, or 2-methyl-2-ketopentanoate may then be converted, via chain elongation, to a $C_7$-$C_{11}$ 2-ketoacid, by the action of various enzymes in the "+1" pathway (or in the LeuABCD pathway, as it is termed with respect to the E. coli microbial organism), as previously described herein.

Referencing FIG. 1, the iterative part of the "+1" pathway (or the iterative part of the LeuABCD pathway in E. coli) is a portion of the non-natural leucine pathway. In embodiments, the enzymes capable of accomplishing chain elongation are identified herein as: isopropylmalate synthase, e.g., a wild type 2-isopropylmalate synthase (such as LeuA; GenBank:Accession No. NC 000913.3 Gene ID: 947465) and/or a genetically modified isopropylmalate synthase having isopropylmalate synthase activity (such as LeuA', e.g., as described by Marcheschi et al. A synthetic recursive "+1" pathway for carbon chain elongation. ACS chemical biology 2012, 7, 689-697, which is incorporated by reference in its entirety); isopropylmalate dehydrogenase, e.g., a wild type isopropylmalate dehydrogenase (such as LeuB; GenBank: Accession NO. NC 000913.3 Gene ID: 944798) and/or a genetically modified isopropylmalate dehydrogenase having isopropylmalate dehydrogenase activity, (such as LeuB', e.g., as described by Sanghani et al. in International Pub. No. WO/2015/089127A1, which is incorporated by reference in its entirety); and/or a genetically modified isopropylmalate isomerase enzyme complex, e.g., a genetically modified LeuCD' complex as previously described herein. Suitable substrates, including intermediates and end product metabolites thereof, may be added at any point in the LeuABCD pathway (shown in FIG. 1) as is known to one of ordinary skill in the art.

In embodiments, the genetically modified isopropylmalate synthase having isopropylmalate synthase activity is as previously described herein, and/or as described by Marcheschi et. al. A synthetic recursive "+1" pathway for carbon chain elongation. ACS chemical biology 2012, 7, 689-697, which is incorporated by reference in its entirety. In some embodiments, the genetically modified isopropylmalate synthase having isopropylmalate synthase activity includes a LeuA' variant having amino acid substitutions at one or more of the following sites: Phe-47 Leu-73, His-97, Phe-99, Ser-139, Asn-167, Pro-169, Asn-197, and/or Gly-462. One or more of Phe-47 Leu-73, His-97, Phe-99, Ser-139, Asn-167, Pro-169, Asn-197, and/or Gly-462; these sites may be substituted with amino acids chosen from glycine, alanine, leucine, and/or valine. Such amino acid substitutions can be performed as previously described herein, such as, e.g., via site-directed mutagenesis. Specifically, site-directed mutagenesis of a known isopropylmalate synthase gene, such as, e.g., LeuA of E. coli (GenBank: Accession No. NC_000913.3 Gene ID: 947465), may be performed to achieve various amino acid substitutions.

In some embodiments, genetically modified LeuA' includes the following specifically contemplated substitutions: alanine for His-97, glycine for Ser-139, glycine for Asn-167, alanine for Pro-169, and/or aspartic acid for Gly-462. Genetically modified LeuA' (i.e., variants) having such specifically contemplated substitutions are believed to be more efficient (higher $k_{cat}/K_m$) than wild type LeuA in capturing 2-ketoacids of interest for catalysis. Thus, without being bound by the theory, it is believed that use of genetically modified LeuA' variants having such specifically contemplated substitutions can improve the overall efficiency of the relevant "+1" pathway.

In embodiments, the genetically modified isopropylmalate dehydrogenase having isopropylmalate dehydrogenase activity is as described by Sanghani et al. in International Pub. No. WO/2015/089127A1, which is incorporated by reference in its entirety. In some embodiments, the genetically modified isopropylmalate dehydrogenase having isopropylmalate dehydrogenase activity includes a LeuB' variant having substitutions at one or more of the following sites: Leu-96 and/or Val-198. One or more of Leu-96 and/or Val-198 may be substituted with the amino acids chosen from glycine, alanine, and/or valine. Such amino acid substitutions can be performed as previously described herein, such as, e.g., via site-directed mutagenesis. Specifically, site-directed mutagenesis of a known isopropylmalate dehydrogenase gene, such as, e.g., LeuB of E. coli (GenBank: Accession No. NC_000913.3 Gene ID: 944798), may be performed to achieve various amino acid substitutions. In some embodiments, the genetically modified LeuB' includes the following specifically contemplated substitutions: glycine or alanine for Leu-96 and/or glycine or alanine for Val-198. Genetically modified LeuB' variants having such specifically contemplated substitutions are believed to be more efficient (higher $k_{cat}/K_m$) than wild type LeuB in converting 3-HM to the corresponding $C_7$-$C_{11}$ 2-ketoacid. Thus, without being bound by the theory, it is believed that use of genetically modified LeuB' variants having such specifically contemplated substitutions can improve the overall efficiency of the relevant "+1" pathway.

Following chain elongation of the 2-ketobutyrate, 2-ketoisolvalerate, or 2-methyl-2-ketopentanoate, the $C_7$-$C_{11}$ 2-ketoacid may be converted to a $C_6$-$C_{10}$ aldehyde by the action of at least one enzyme, such as a thiamin dependent decarboxylase (e.g., a wild type and/or genetically modified thiamin dependent decarboxylase having decarboxylase activity). Specifically, the 2-ketobutyrate, 2-ketoisovalerate, or 2-methyl-2-ketopentanoate may be provided and/or contacted with a wild type and/or genetically modified thiamin dependent decarboxylase having decarboxylase activity. In embodiments, the wild type and/or genetically modified thiamin dependent decarboxylase acts via converting $C_7$-$C_{11}$ 2-ketoacids to $C_6$-$C_{10}$ aldehydes having one less carbon atom than the $C_7$-$C_{11}$ 2-ketoacids being converted. In embodiments, the thiamin dependent decarboxylase has thiamin dependent decarboxylase activity. Further disclosure regarding the modification and selection of thiamin dependent decarboxylase having thiamin dependent decarboxylase activity is included in co-pending International Publication No. WO/2015/089127, which is incorporated herein in its entirety by reference.

The $C_6$-$C_{10}$ aldehydes may be used in a variety of industrial applications and/or employed as intermediates and/or starting material for production of different chemicals. For example, the $C_6$-$C_{10}$ aldehydes may be provided and/or contacted with an alcohol dehydrogenase, e.g., a wild type (Accession No. NC_001145.3, GeneID:855368) and/or a genetically modified alcohol dehydrogenase, which converts the $C_6$-$C_{10}$ aldehydes to corresponding $C_6$-$C_{10}$ alcohol products. In embodiments, the alcohol dehydrogenase has alcohol dehydrogenase activity. Alternatively, the $C_6$-$C_{10}$ aldehydes may be provided and/or contacted with an aldehyde dehydrogenase, e.g., a wild type and/or genetically modified aldehyde dehydrogenase (Accession No. NM_000689.4), which converts the $C_6$-$C_{10}$ aldehydes to corresponding $C_6$-$C_{10}$ carboxylic acid products. In embodiments, the aldehyde dehydrogenase has aldehyde dehydrogenase activity. Finally, the $C_6$-$C_{10}$ aldehydes may be contacted with a fatty aldehyde decarbonylase, e.g., a wild type and/or genetically modified fatty aldehyde decarbonylase (Accession No. NM_100101.3), which converts the $C_6$-$C_{10}$ aldehydes to corresponding $C_{n-1}$ alkane products. In embodiments, the fatty aldehyde decarbonylase has fatty aldehyde decarbonylase activity. In some embodiments, the $C_5$-$C_{10}$ alcohol, carboxylic acid, or alkane products described previously herein, for example, $C_6$-$C_{10}$ alcohols, $C_6$-$C_{10}$ carboxylic acids, and/or $C_5$-$C_9$ alkanes, are produced with high specificity. For example, the $C_5$-$C_{10}$ alcohol, carboxylic acid, and/or alkane products can be produced as about 25 wt %, at about 40 wt %, at about 50 wt %, or at about 70 wt % or more, of the total product.

In embodiments, the processes for preparing a $C_7$-$C_{11}$ 2-ketoacid further include converting the $C_7$-$C_{11}$ 2-ketoacid, with additional enzymes and biochemical reactions, to a desired $C_6$-$C_{10}$ aldehyde, $C_6$-$C_{10}$ alcohol, $C_6$-$C_{10}$ carboxylic acid, and/or $C_5$-$C_9$ alkane. These processes may be carried out biosynthetically in one of the described embodiments of a non-naturally occurring, i.e., genetically engineered, cell. For example, in illustrative, non-limiting embodiments, these processes may be carried out in a non-naturally occurring microbial organism, as previously described herein. In other illustrative, non-limiting embodiments, production of the $C_7$-$C_{11}$ 2-ketoacids, $C_6$-$C_{10}$ aldehydes, $C_6$-$C_{10}$ alcohols, $C_6$-$C_{10}$ carboxylic acids, and/or $C_5$-$C_9$ alkanes may be carried out via in vitro methodology, such as, e.g., beginning from a starting point that does not include a microbial organism.

In some embodiments, processes for preparing a $C_7$-$C_{11}$ 2-ketoacid further include: (II) providing the $C_7$-$C_{11}$ 2-ketoacid with a thiamin dependent decarboxylase having thiamin dependent decarboxylase activity (e.g., a wild type and/or genetically modified thiamin dependent decarboxylase having thiamin dependent decarboxylase activity), under conditions the $C_7$-$C_{11}$ 2-ketoacid is converted to a $C_6$-$C_{10}$ aldehyde having one less carbon atom than the $C_7$-$C_{11}$ 2-ketoacid being converted.

In further embodiments, the processes for preparing a $C_7$-$C_{11}$ 2-ketoacid further include: (III) providing the $C_6$-$C_{10}$ aldehyde with an alcohol dehydrogenase having alcohol dehydrogenase activity (e.g., a wild type and/or genetically modified alcohol dehydrogenase having alcohol dehydrogenase activity), under conditions that the $C_6$-$C_{10}$ aldehyde is converted to a corresponding $C_6$-$C_{10}$ alcohol. In some embodiments, the processes for preparing a $C_7$-$C_{11}$ 2-ketoacid further include: (III) providing the $C_6$-$C_{10}$ aldehyde with an aldehyde dehydrogenase having aldehyde dehydrogenase activity (e.g., a wild type and/or genetically modified aldehyde dehydrogenase having aldehyde dehydrogenase activity), under conditions that the $C_6$-$C_{10}$ aldehyde is converted to a corresponding $C_6$-$C_{10}$ carboxylic acid. In some embodiments, the processes for preparing a $C_7$-$C_{11}$ 2-ketoacid further include: (III) providing the $C_6$-$C_{10}$ aldehyde with a fatty aldehyde decarbonylase having fatty aldehyde decarbonylase activity (e.g., a wild type and/or genetically modified fatty aldehyde decarbonylase having fatty aldehyde decarbonylase activity), under conditions that the $C_6$-$C_{10}$ aldehyde is converted to a corresponding $C_{n-1}$ alkane.

The processes for preparing a $C_7$-$C_{11}$ 2-ketoacid may be carried out either in vivo or in vitro. Both an in vivo approach and an in vitro approach may be useful for commercial scale production, depending on the circumstances. In some embodiments, an in vitro approach is useful for laboratory and/or research purposes, such as, e.g., to carry out enzymatic assays. With both in vivo and in vitro approaches, a suitable microbial organism as previously described herein may be utilized.

Embodiments of processes for preparing $C_7$-$C_{11}$ 2-ketoacids with genetically modified isopropylmalate isomerase enzyme complexes have been described in detail.

EXAMPLES

Example 1: Preparing the Genetically Modified LeuCD' Enzyme Complexes Having Increased Activity Against 2-Hexylmalate (2-HM)

During 2-ketononanoate biosynthesis by the recursive activity of the LeuABCD pathway, 2-alkylmalic acids of varying lengths are formed as substrates of LeuCD. For efficient biosynthesis of 2-ketononanoate, it is desired that LeuCD efficiently capture 2-ethylmalate (intermediate II, n=1; FIG. 1), 2-propylmalate (2-IPM; Intermediate II, n=2; FIG. 1), 2-butylmalate (Intermediate II, n=3; FIG. 1), 2-pentylmalate (Intermediate II, n=4; FIG. 1) and 2-hexylmalate (2-HM; Intermediate II, n=5; FIG. 1) for catalysis. The wild type LeuCD is relatively inefficient in capturing longer non-natural 2-alkylmalate substrates. To improve the efficiency of wild type LeuCD in capturing 2-hexylmalate for catalysis, the active site of wild type LeuCD enzyme complex was modified using protein engineering techniques as described subsequently.

Figure 3:
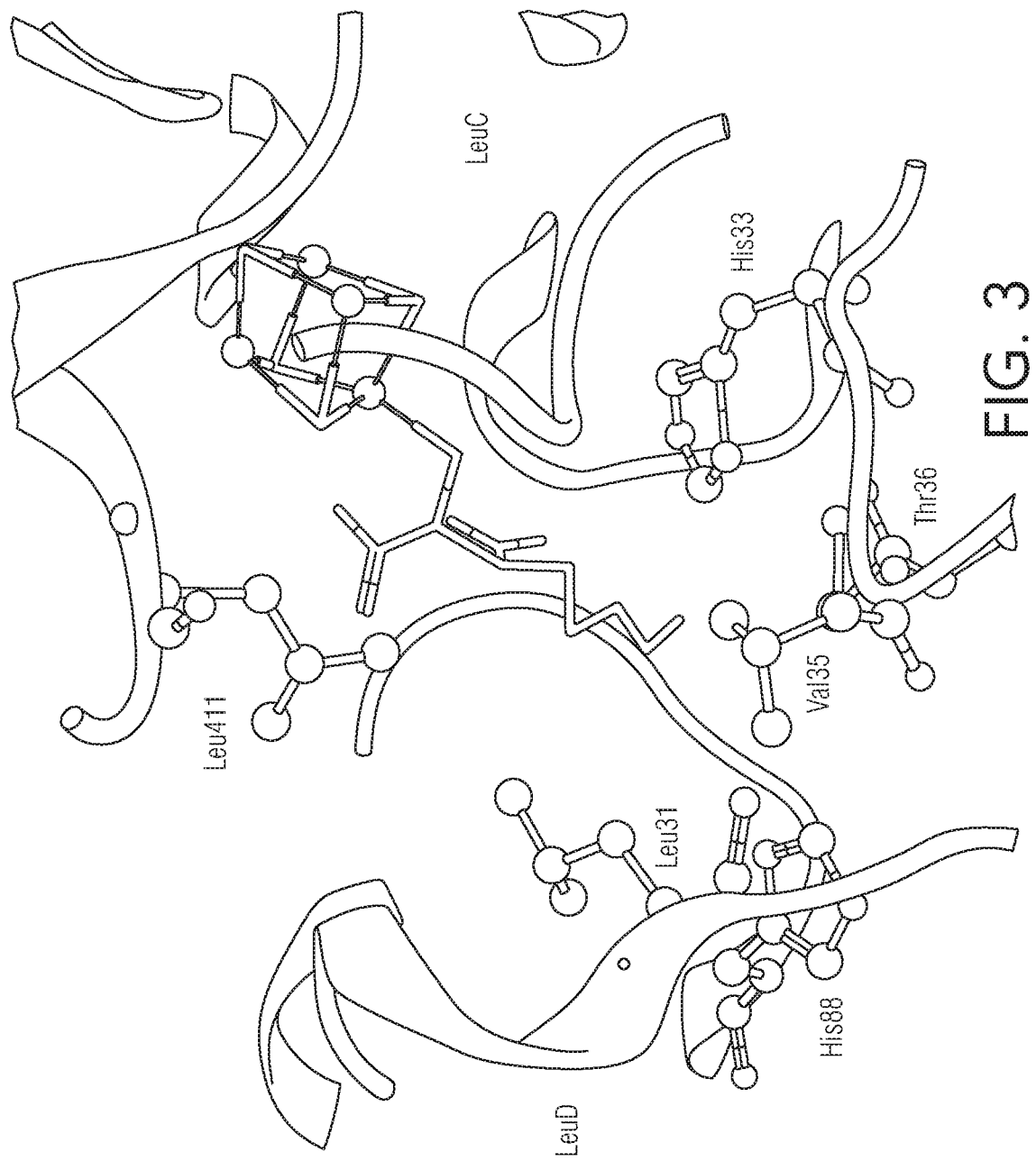
FIG. 3. Homology model of the LeuCD active site.

*E. coli* isopropylmalate isomerase (i.e., LeuCD) is a heterodimer made up of a 50 kDa subunit called LeuC and a 22.4 kDa subunit called LeuD. Both subunits come together to form a functional enzyme having the active site at the dimer interface. Residues lining the 2-isopropylmalate binding site of *E. coli* LeuCD were identified from a structural model of LeuCD (that was constructed via homology modeling and using as the template the crystal structure model of pig aconitase (Protein Data Bank (PDB) code 1ACO) and isopropylmalate isomerase small unit of *Campylobacter jejuni* (PDB ID code 3Q3W) (FIG. 3). Initially, models of the LeuC and LeuD subunits were constructed separately using the molecular modeling program MOE (Chemical Computing Group Inc. Montreal Canada), and the pig aconitase (PDB code 1ACO) and the small subunit of *Campylobacter jejuni* (PDB ID code 3Q3W) as templates, respectively. The functional complex was generated by overlaying both the subunit models on the two domains of aconitase. The 4Fe-4S cluster and the transaconitase present in the active site of pig aconitase crystal structure model were used as templates to build a kinetically competent model of LeuCD with substrates, 2-isopropylmalate and 2-hexylmalate, bound within the active site. Residues Val-35 and Leu-411 in LeuC and Leu-31 and His-88 in LeuD were found to be near the isopropyl and hexyl group of the substrates, and were selected for modification (FIG. 2). Each of these residues was modified to an amino acid residue with smaller hydrophobic side chain to make room for the bulkier alkyl group. As shown in Table 1, 15 variants were designed for evaluation.

The variants were initially tested for activity against a single high concentration of 2-IPM, 2-BM and 2-HM. The assay involved coupling the LeuCD reaction with that of the LeuB reaction. Thus, during the assay, 2-IPM was initially isomerized to 3-isopropylmalate (3-IPM) by LeuCD which was immediately converted to 4-methyl-2-ketovalerate by the LeuB enzyme present in the assay mixture. Likewise, in the assays involving 2-BM or 2-HM as substrates, the end product formed in the assay was 2-ketoheptanoate or 2-ketononanoate, respectively. The activity of LeuCD variant was calculated from the amounts of respective 2-ketoacids produced in the coupled assay. LeuCD' variants that have higher activity than the wild type enzyme in converting all or some of the 2-alkylmalate substrates, such as 2-HM, to the corresponding $C_7$-$C_{11}$ 2-ketoacid, are desirable because they improve the overall efficiency and avoid bottlenecking of the relevant "+1" LeuABCD pathway of FIG. 1. Following the initial evaluation, a more detailed kinetic analysis was performed on a select number of LeuCD variants to determine the maximal rate (i.e., $k_{cat}$), Michaelis-Menten constant (i.e., $K_M$), and the catalytic efficiency of the enzyme (i.e., $k_{cat}/K_M$) for some of the substrates.

Example 2: Expression of LeuCD Variants in *E. coli*

To evaluate the substrate specificity of the wild type LeuCD and the engineered LeuCD' variants listed in Table

TABLE 1

LeuCD variants generated by coexpressing various LeuC and LeuD subunits and activity of LeuCD variants.

| Variant | | | Activity, pmol · min$^{-1}$ · μg$^{-1}$ | | |
|---|---|---|---|---|---|
| No. | LeuC subunit | LeuD subunit | 2-IPM | 2-BM | 2-HM |
| 3 | Wt LeuC | Wt LeuD | 368 ± 6.2 | 1247 ± 1 | 0.63 ± 0.01 |
| 1 | V35A | Wt LeuD | 1.3 ± 0.0 | 52 ± 1 | 40 ± 0.8 |
| 5 | Wt LeuC | L31A | 1.7 ± 0.0 | 245 ± 4 | 6.2 ± 0.2 |
| 6 | Wt LeuC | L31G | 0.0 ± 0.0 | 30 ± 1 | 215 ± 6.4 |
| 9 | V35A | L31G | 0.0 ± 0.0 | 1.7 ± 0.0 | 51 ± 1.4 |
| 10 | V35G | L31V | 0.7 ± 0.0 | 11 ± 0.3 | 2.4 ± 0.1 |
| 18 | L411V | L31G | 0.0 ± 0.0 | 1.3 ± 0.0 | 12 ± 0.0 |
| 31 | V35A/L411V | L31V | 4.7 ± 0.3 | 54 ± 1.2 | 2.8 ± 0.1 |
| 32 | V35A/L411V | L31A | 0.0 ± 0.0 | 4.7 ± 0.1 | 3.1 ± 0.2 |
| 35 | V35A/L411A | L31A | 0.0 ± 0.0 | 0.6 ± 0.0 | 0.4 ± 0.00 |
| 36 | V35A/L411A | L31G | 0.0 ± 0.0 | 0.0 ± 0.0 | 0.84 ± 0.01 |
| 38 | V35A/L411G | L31A | 0.0 ± 0.0 | 1.0 ± 0.0 | 0.6 ± 0.01 |
| 39 | V35A/L411G | L31G | 0.0 ± 0.0 | 0.0 ± 0.0 | 3.1 ± 0.0 |
| 59 | Wt LeuC | L31V/H88A | 1.2 ± 0.0 | 33 ± 1.0 | 27.4 ± 0.2 |
| 61 | Wt LeuC | L31G/H88A | 0.0 ± 0.0 | 1.2 ± 0.0 | 11.6 ± 0.2 |
| 64 | Wt LeuC | L31G/H88S | 0.0 ± 0.0 | 0.8 ± 0.0 | 7.5 ± 0.1 |
| 115 | V35G/L411V | L31A/H88S | 0.0 ± 0.0 | 0.0 ± 0.0 | 1.4 ± 0.02 |

*LeuC and LeuD subunits were identified by the modifications made to the wild type amino acid sequence. The notation for these specific genetic modifications, as well as similar notations for genetic modifications disclosed throughout this disclosure, adhere to industry standard wherein amino acid modifications are defined as the original single letter amino acid code, followed by the amino acid position, followed by the new amino acid single letter code. L = leucine; A = alanine; G = glycine; V = valine; S = serine; and I = isoleucine.

Each of the engineered LeuCD variants was expressed, isolated, and then evaluated without further purification for activity against 2-isopropylmalate (i.e., 2-IPM), 2-butylmalate (i.e. 2-BM) and 2-hexylmalate (i.e., 2-HM), as described subsequently. 2-IPM is the natural substrate of LeuCD and is formed in microbial organisms during the biosynthesis of leucine. 2-BM and 2-HM are non-natural substrates of LeuCD that would be formed inside cells during $C_7$-$C_{11}$ 2-ketoacid, for example, 2-ketononanoate, biosynthesis.

The evaluation of the LeuCD' variants was performed in two steps using the enzyme assay described subsequently.

1, genes of each complex were expressed into *E. coli* cells separately. The gene sequences of LeuC (EcoGene Accession No. EG11576 (Sequence Listing, SEQ ID 1) and LeuD (EcoGene Accession No. EG11575) were downloaded from the *E. coli* genome website, EcoGene (http://ecogene.org). Codons of 13 additional amino acids that included six histidines were fused upstream of the codon of Met-1 of LeuC gene sequence. Such a modification allowed expression of a His-tagged LeuC having 13 additional amino acids on the N-terminus. To the resulting modified gene, additional bases were added to introduce a NcoI and a SacI restriction site at the 5'- and 3'-end, respectively, for cloning purposes. The whole DNA sequence was chemically synthesized and cloned into an *E. coli* expression vector, pRSFDuet-1 (purchased from EMD Biosciences) at the NcoI and SacI sites by SGI Inc. To the downloaded LeuD gene sequences, additional bases were added to introduce a NdeI and XhoI restriction sites at the 5'- and 3'-end, respectively. The resulting modified gene was also chemically synthesized and cloned into an *E. coli* expression vector, pETDuet-1 vector, at the NdeI and XhoI restriction sites by SGI Inc. The genes of the additional LeuC and LeuD variants were also chemically synthesized and cloned into the pRSFDuet and pETDuet vectors, respectively Fully functional isopropylmalate isomerase (i.e., LeuCD) was produced in *E. coli* BL21(DE3) (purchased from EMD Biosciences) cells by cotransfecting them with individual LeuC and LeuD subunit expressing vectors. Different LeuCD variants were produced by cotransfecting different combinations of LeuC and LeuD variant vectors in *E. coli* cells. Table 1 shows the LeuC and LeuD vector combination that was used for producing corresponding LeuCD variant in *E. coli*. It is noted that none of the Sequence Listings included herein show the histidine-tag that is used, which in this case is Gly-Ser-Ser-His-His-His-His-His-His-Ser-Ser.

Cotransfection of the *E. coli* BL21(DE3) cells with the LeuC and LeuD expression vectors was performed using standard procedures. Cells harboring the expression vectors were selected on LB agar plates containing 100 µg/mL of ampicillin and 50 µg/mL of kanamycin. A starter culture was started by transferring a single colony of transformant into 50 mL of LB medium containing 100 g/mL of ampicillin and 50 µg/mL of kanamycin and incubated at 37° C. with shaking at 220 rpm overnight. On the next day, 7 mL of starter culture was inoculated into 800 mL of Terrific Broth (TB) and the culture was incubated at 37° C. until it reached an $OD_{600\ nm}$ of 0.5. Isopropyl β-D-1-thiogalacto-pyranoside (IPTG) at a final concentration of 1 mM was added to induce the expression of the LeuCD complex or its variant and the culture was transferred to a 15° C. incubator for 16 hours (h). At the end of 16 h, the culture was centrifuged at 8000 revolutions per minute (rpm) to pelletize the cells. The cell pellet was divided into four aliquots and stored at −80° C. until disruption for the isolation of the LeuCD complex.

The LeuCD complex was isolated from the cell pellet in an anaerobic chamber (acquired from COY Lab Products (MI, USA)) maintained under 98% nitrogen and 2% Hydrogen. The *E. coli* pellet was suspended in 50 mM HEPES buffer (pH 8.0) containing 0.2 mM ferrous ammonium sulfate, 10 mM DTT, 30 mM KCl, 5 mM $MgCl_2$ and protease inhibitor cocktail (acquired from SIGMA-ALDRICH, USA). To the cells, 2.5 gm of 0.1 mm glass beads were added and the cells were disrupted on a Geno grinder for 3 minutes at 1750 rpm. Cell debris and the glass beads were pelleted by centrifugation and the supernatant was mixed with equal volume of 50% glycerol and stored anaerobically at −20° C.

Functional evaluation of each LeuCD variant was performed using the whole cell lysate from the cells in which it was produced. For comparing the catalytic efficiencies of each LeuCD complex, the amounts of LeuC and LeuD variant in the whole cell lysate was determined using microfluidic capillary electrophoresis on Labchip GX II (Perkin Elmer Inc., Waltham, Mass.) equipped with a fluorescent detector. Cell lysates were prepared for capillary electrophoresis using the manufacturer supplied reagents and protocol. Briefly, 4 µL aliquots of the cell extract was mixed with 14 µL of denaturing buffer. The mixture was heated at 100° C. for 5 minutes and were allowed to cool to room temperature. After cooling, 70 µL sterile water was added to the mixture and was analyzed using the protocol supplied by PerkinElmer. LabChip GX II software analyzed and reported the size, relative concentration and purity of the LeuC and LeuD detected in each sample. Cell extracts from cells containing empty vectors served as a negative control for identification of LeuC and LeuD proteins in the extracts. Analytical grade Bovine Serum Albumin (BSA) standard solution (2 mg/mL) supplied by Pierce Biotechnology (Rockford, Ill.) was used as standard for quantification. In all the LeuCD complex containing extracts, LeuC subunit was the limiting subunit. The activity of each LeuCD extract was normalized with respect to the amount of LeuC present in the extract.

Example 3: Determination of the Substrate Specificity of the Wild Type and the Engineered LeuCD' Variants A high-throughput LeuCD enzyme assay was developed for the screening and kinetic evaluation of LeuCD' variants, as prepared in Examples 1 and 2, for activity against 2-isopropylmalate (i.e., 2-IPM), 2-butylmalate (2-BM) and 2-hexylmalate (i.e., 2-HM). The coupled assay involved coupling the LeuCD reaction with that of the LeuB reaction. Thus, during the assay, 2-IPM was initially isomerized to 3-isopropylmalate (3-IPM) by LeuCD which was immediately converted to 4-methyl-2-ketovalerate by the LeuB enzyme present in the assay mixture. Likewise, in the assays involving 2-BM or 2-HM as substrates, the end product formed in the assay was 2-ketoheptanoate or 2-ketononanoate, respectively. The activity of LeuCD variant was calculated from the amounts of respective 2-ketoacids produced in the coupled assay.

The HTP LeuCD coupled assay used for screening the activity of each variant involved incubating the whole cell lysate from cells expressing the LeuCD variant with 2.6 mM 2-isopropylmalate (i.e., 2-IPM), 2-butylmalate (i.e., 2-BM) or 2-hexylmalate (i.e., 2-HM), in a mixture containing: 20 µg of wild type LeuB, 16 µg of a L96G/V198A variant of LeuB, 5 mM $NAD^+$, 10 mM DTT, 20 µg bovine serum albumin, 30 mM KCl, 5 mM $MgCl_2$, and 50 mM HEPES pH 8. The total assay volume was 100 µL and was performed anaerobically in a COY chamber at room temperature for a period of 1 hr. The reaction was stopped by the addition of an equal volume of a mixture containing 20% formic acid and 10% methanol. The 2-ketoacids formed in the coupled assay were quantitated using an Agilent 1290 Infinity uHPLC coupled with an AB Sciex 5500 QTrap mass spectrometer. Following the separation of the 2-ketoacids on Waters Acquity HSS T3 1.8 µM 3.0×150 mm reverse phase column under reverse phase conditions, the detection and quantitation was performed in the mass spectrometer by single quadrupole select ion monitoring method that operated in negative mode. Quantitation was based off an external calibration curve generated for each 2-ketoacid from custom synthesized analytical grade standard reference material with the exception of 4-methyl-2oxovalerate which was commercially available from Sigma-Aldrich.

The activities were normalized with the amounts of LeuC subunit in the whole cell lysate. 2-IPM is the native substrate of LeuCD and activity against it would indicate that the engineered enzymes would be able to catalyze the earlier cycles of "+1" pathway during 2-ketobutyrate elongation to 2-KN. 2-BM and 2-HM are the non-native substrates of LeuCD. LeuCD variants having higher activity against 2-HM than the wild type LeuCD would be capable of improving octanol yield by making the later cycles of "+1" pathway during 2-KN formation more efficient. The HTP assay involved coupling of the LeuCD activity with that of the next enzyme in the "+1" LeuABCD pathway, isopropylmalate dehydrogenase (i.e., LeuB). Thus, 3-isopropylmalate (i.e., 3-IPM), 3-butylmalate or 3-hexylmalate (i.e., 3-HM) produced from 2-IPM, 2-BM or 2-HM, respectively, by LeuCD were oxidatively decarboxylated by LeuB to 2-ketoisocaproate, 2-ketoheptanoate and 2-ketononanoate (i.e., 2-KN). All three 2-ketoacids were then quantitated using LC/MS.

As shown in Table 1, the wild type LeuCD (Variant 3) is highly active against 2-IPM and 2-BM, while having very little activity against 2-HM. Table 1 also highlights that 13 LeuCD variants had 2-340 fold higher activity than the wild type LeuCD in isomerizing 2-hexylmalate to 3-hexylmalate. Residue Val-35 within the LeuC subunit and Leu-31 within LeuD had a major impact on improving the activity against 2-HM. For example, Variants 1 (i.e., V35A-LeuC+wt LeuD) and 6 (i.e., wt LeuC+L31G-LeuD), respectively had 63- and 341-fold higher activity against 2-HM than the wild type LeuCD (i.e., Variant 3). While the V35A and L31G substitutions in LeuC and LeuD, respectively increased the activity against 2-HM, they significantly diminished activity against 2-IPM. Together, the data indicate that Variants 1 and 6 would be significantly less effective than the wild type enzyme in the earlier cycles of "+1" pathway during the elongation of 2-ketobutyrate, but will be 60- to 350-fold more efficient during later stages of elongation of 2-ketobutyrate. Expressing both the wild type LeuCD and Variant 1 or Variant 6 would improve the elongation of 2-ketobutyrate to $C_7$-$C_{11}$ 2-ketoacids and eventually, $C_6$-$C_{10}$ alcohols.

Example 4: Determination of the Catalytic Efficiencies of the LeuCD Variants Showing High Specificity for 2-Hexylmalate (2-HM)

Following the initial evaluation, a more detailed kinetic analysis was performed on the wild type LeuCD and a select number of variants to determine the maximal rate (i.e., $k_{cat}$), Michaelis-Menten constant (i.e., $K_M$), and the catalytic efficiency of the enzyme (i.e., $k_{cat}/K_M$) for 2-IPM, 2-BM and 2-HM. The kinetic determinations were performed using the HTP enzyme assay described previously, with minor modifications. During the kinetic parameter determinations, 2-IPM, 2-BM, and 2-HM concentrations were varied from 0-0.625 mM, 0-5 mM, and 0-1.6 mM, respectively. The assay was carried out for 30 min and the amount of wild type or LeuCD variant extract was adjusted to limit substrate consumption below 20%. For the maximal rate ($k_{cat}$) calculations, the amount of LeuCD complex present in the enzyme reaction was determined on the basis of the amount of LeuC determined using the microfluidic capillary electrophoresis on Labchip GX II (Perkin Elmer Inc., Waltham, Mass.). The kinetic parameters were calculated by fitting the activity in the assay to Michaelis-Menton equation using the Graphpad Prizm software.

TABLE 2

Kinetic parameters of LeuCD complexes.

| | 2-IPM | | | 2-BM | | | 2-HM | | |
|---|---|---|---|---|---|---|---|---|---|
| Variant | $k_{cat}$, hr$^{-1}$ | $K_M$, mM | $k_{cat}/K_M$, mM$^{-1}$hr$^{-1}$ | $k_{cat}$, hr$^{-1}$ | $K_M$, mM | $k_{cat}/K_M$, mM$^{-1}$hr$^{-1}$ | $k_{cat}$, hr$^{-1}$ | $K_M$, mM | $k_{cat}/K_M$, mM$^{-1}$hr$^{-1}$ |
| 3 | 1526 ± 58 | 0.068 ± 0.01 | 22366 ± 2375 | 6120 ± 323 | 1.33 ± 0.14 | 4646 ± 554 | | | 4 ± 1 |
| 1 | | | | 542 ± 83 | 3.9 ± 0.7 | 145 ± 34 | 314 ± 55 | 3.35 ± 0.75 | 98 ± 28 |
| 5 | | | | 1400 ± 77 | 1.31 ± 0.14 | 1077 ± 129 | 35 ± 5 | 1.4 ± 0.6 | 29 ± 13 |
| 6 | | | | 477 ± 120 | 8.44 ± 2.4 | 62 ± 24 | 1237 ± 34 | 0.65 ± 0.04 | 1917 ± 129 |
| 9 | | | | | | 2 ± 0.0 | 166 ± 5 | 0.6 ± 0.034 | 283 ± 18 |
| 59 | | | | 218 ± 22 | 2.7 ± 0.4 | 83 ± 14 | 182 ± 37 | 3.8 ± 0.9 | 50 ± 16 |
| 61 | | | | | | 1.0 ± 0.0 | | | 22 ± 2 |

As highlighted in Table 2, the wild type LeuCD complex (Variant 3) is highly efficient in catalyzing its natural substrate, 2-IPM. The wild type enzyme preferred its non-natural substrates, 2-BM and 2-HM, less as evident by their lower kcat/KM values. 2-HM was the least preferred substrate. Variants 1, 5, 6, 9, 59 and 61 showed from 5- to 480-fold improvement in catalytic efficiency for 2-HM over the wild type enzyme. The kinetic data also show that variant 5 was more efficient (kcat/KM) at catalyzing isomerization of 2-BM than that of 2-HM while Variants 6, 9 and 61 were more efficient in catalyzing 2-HM over 2-BM. Variants 1 and 59 showed very similar efficiencies in catalyzing the isomerizations of 2-BM and 2-HM.

Example 5: In Vivo Production of $C_4$-$C_8$ Alcohols in Engineered Strains of E. coli Using Wild Type LeuCD and its Variants in Combination with the '+1 Pathway' Enzymes Strain Construction The effects of LeuCD variants on alcohol production was evaluated in an engineered MG1655 strain of *Escherichia coli* (*E. coli*). The MG1655 strain was modified to improve linear alcohol production, enable expression of the genes from the Plac promoters and impart clonal stability. Improvements for linear alcohol production involved knocking down of the ilvBN and ilvIH genes, and upregulation of the ilvA gene in *E. coli* MG1655. Knock-out of ilvBN and IlvIH genes eliminated branched chain alcohol production, while upregulation of the ilvA gene increased the production of 2-ketobutyrate. Upregulation of ilvA was effected by replacing its native promoter and ribosome binding site with a strong constitutive promoter, BBa_J23119 and a synthetic ribosome binding site, BBa_B0034. Both the strong constitutive promoter and the synthetic ribosome binding site were obtained from the Registry of Standard Biological Parts (http://parts.igem.org), a database of biological parts curated by iGEM (International Genetically Engineered Machine Competition). The knocking out of the ilvBN and ilvIH genes and the replacement of the native promoter and ribosome binding site of ilvA gene was performed via lambda(red)-mediated recombination as described by Datsenko and Wanner (PNAS 97(12):6640-6645). To enable expression of the genes from the Plac promoters, the DE3 lysogen was integrated into MG1655 using the 2DE3 Lysogenization Kit (EMD Millipore Cat #69734). To ensure clonal stability, recA was inactivated by λRed-mediated homologous recombination. The genotype of the resulting strain that was used for the alcohol production studies was MG1655(DE3) ΔrecA ΔilvBN ΔilvIH ilvAup.

Vector Construction

Figure 7:
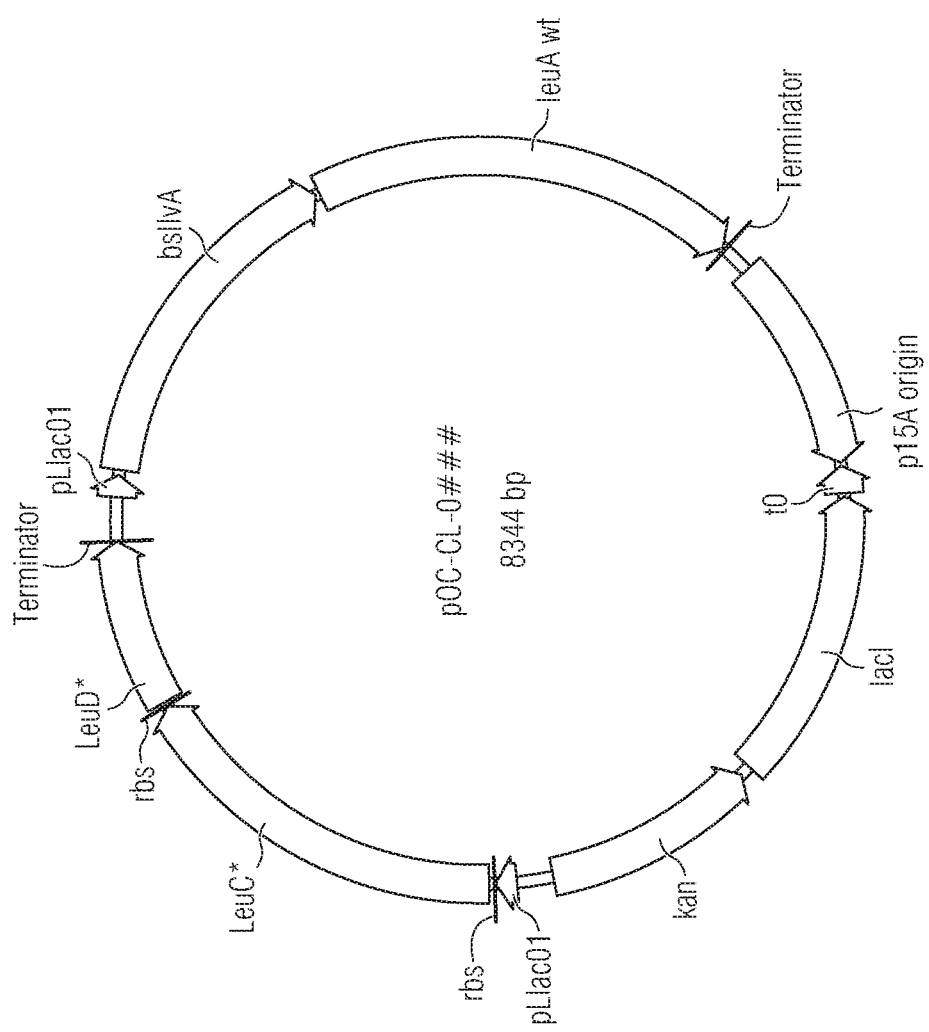
FIG. 7. The pOC-CL-0### vector. Shown is a typical modified pOC-CL-### vector that was used with the pZE_LeuABCD-KA6 vector for the alcohol production studies.

During the evaluation of the effects of LeuCD variants on $C_4$-$C_8$ alcohol production in the engineered MG1655 E. coli strain, the following seven enzymes were coexpressed: i) Wild type E. coli isopropylmalate synthase (LeuA; GenBank:Accession No. NC 000913.3 Gene ID: 947465), ii) LeuA* (H97A/S139G/N167G/P169A/G462D variant of E. coli IPMS described by Marcheschi et al ACS Chem. Biol. 2012, 7, 689-697), iii) wild type E. coli isopropylmalate isomerase (LeuCD; GenBank:Accession No. NC 000913.3 Gene ID: 94576 and Gene ID: 945642), iv) isopropylmalate isomerase variants described in Table 3, v) E. coli isopropylmalate dehydrogenase (LeuB; GenBank: Accession NO. NC 000913.3 Gene ID: 944798), vi) F381L/V461A variant of ketoisovalerate decarboxylase (KIVD*) from Lactocossus lactis (described by Zhang et. al PNAS. 2008, 105, 20653-20658), and vii) S. cerevisiae alcohol dehydrogenase (ADH6; GenBank: Accession No. NC_001145.3 GeneID: 855368). All the enzymes were expressed in E. coli using the two expression vectors, pZE_LeuABCD-KA6 and pZAlac_ilvAleuA described by Marcheschi et al (ACS Chem. Biol. 2012, 7, 689-697). pZE_LeuABCD-KA6 was acquired from Dr. Liao's group and used without any further modification. pZE_LeuABCD-KA6 expressed LeuA* (H97A/S139G/N167G/P169A/G462D variant of E. coli IPMS described by Marcheschi et al ACS Chem. Biol. 2012, 7, 689-697), LeuB, LeuC, LeuD, and KiVD* (F381L/V461A variant of ketoisovalerate decarboxylase from Lactocossus lactis described by Zhang et. al PNAS. 2008, 105, 20653-20658) in the engineered MG1655 strain. Vector pZAlac_ilvAleuA, that had a copy of Ilva and wild type LeuA genes, was modified to express the LeuCD variant genes described here. Eleven vectors containing the LeuC and LeuD variant genes as shown in Table 3 were constructed for the evaluation of the effects on alcohol composition in the engineered MG1655 strain. FIG. 7 shows a typical modified vector, pOC-CL-0###, that was used along with pZE_LeuABCD-KA6 for the alcohol production studies. As shown in FIG. 7 and listed in Table 3, each pOC-CL-0### vector had a LeuC* and LeuD* gene that expressed a given LeuCD variant, a wild type E. coli isopropylmalate isomerase, and the ilvA gene protein. All the genes in both the vectors were under pLacO1 promoter and induced using Isopropyl β-D-1-thiogalactopyranoside (IPTG).

Figure 6:
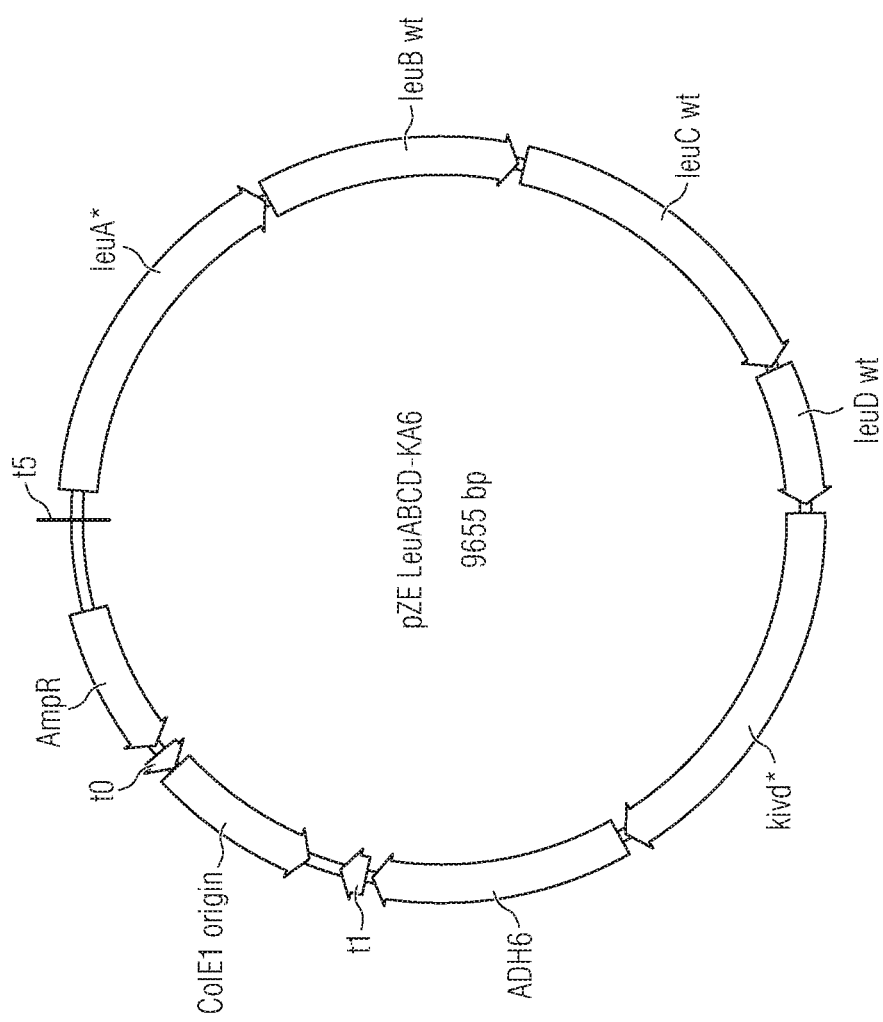
FIG. 6. The pZE_LeuABCD-KA6 vector. Shown is the pZE_LeuABCD-KA6 vector that was used with a modified vector, pOC-CL-###, for the alcohol production studies.
Figure 8A:
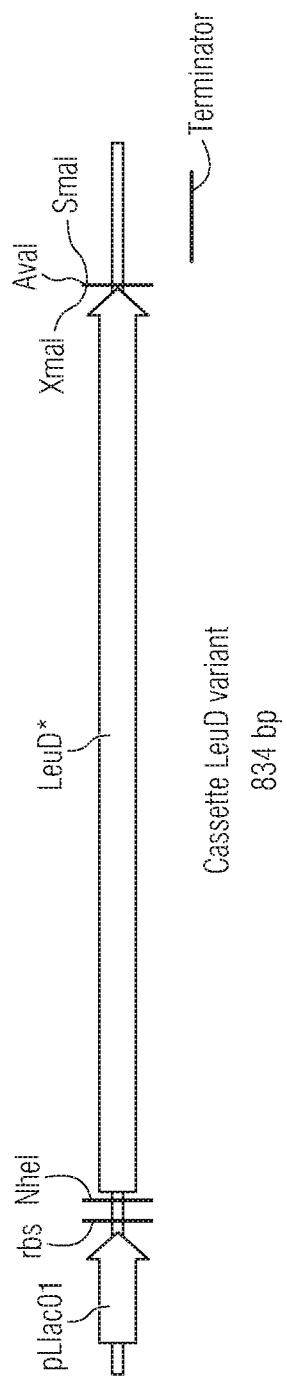
FIGS. 8A-8B. Cassettes for LeuD and LeuC variants.
Figure 8B:
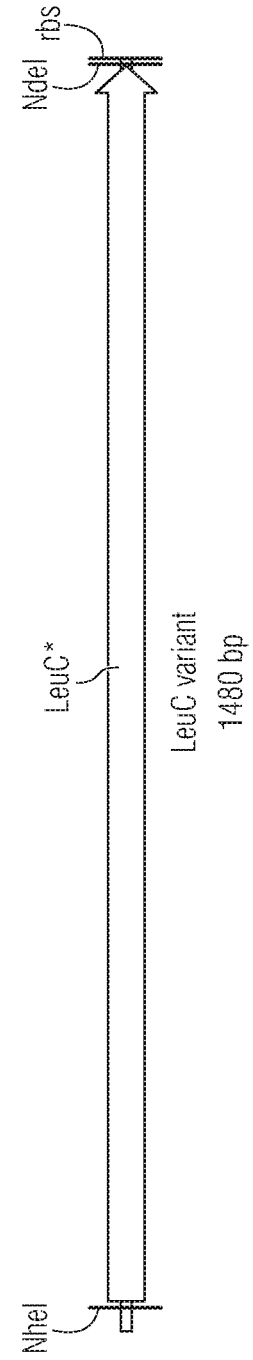

The genes of LeuC and LeuD variants were cloned into the pZAlac_ilvAleuA vector in two steps using the Gibson assembly technology of New England Bioscience. The first step involved insertion of the LeuD variant gene as a cassette (shown in FIG. 8A) at the ZraI site of the pZAlac_ilvAleuA vector. The LeuD variant gene cassette was generated as a Gblock (by Integrated DNA Technologies) and had a placO1 promoter, ribosome binding site (rbs), and a unique NheI site on the 5' side of the LeuD variant gene (FIG. 8A). A terminator sequence and unique restriction sites were placed on the 3'-end of the LeuD variant gene (FIG. 8A). The second step in the vector construction involved introduction of the LeuC variant gene as a PCR generated cassette (FIG. 8B) using the Gibson assembly technology. The arrangement of genes in the final resulting vector as identified by the pOC-CL-0### vector is shown in FIG. 2. For alcohol production, the engineered MG1655 strain of E. coli (MG1655(DE3)) ΔrecA ΔilvBN ΔilvIH ilvAup) was transformed with the pZE_LeuABCD-KA6 vector (FIG. 6) containing the full pathway and one of the pOC-CL-0### vector listed in Table 3.

TABLE 3

Vectors containing the LeuC and LeuD variant genes constructed for the evaluation of the effects on alcohol composition in the engineered MG1655 strain.

| Variant | LeuC | LeuD | pOC-CL-0### |
|---|---|---|---|
| 1 | V35A | Wt LeuD | pOC-CL-0122 |
| 2 | V35G | Wt LeuD | pOC-CL-0123 |
| 3 | Wt LeuC | Wt LeuD | pOC-CL-0124 |
| 6 | Wt LeuC | L31G | pOC-CL-0112 |
| 9 | V35A | L31G | pOC-CL-0113 |
| 10 | V35G | L31V | pOC-CL-0127 |
| 38 | V35A/L411G | L31A | pOC-CL-0129 |
| 39 | V35A/L411G | L31G | pOC-CL-0114 |
| 59 | Wt LeuC | L31V/H88A | pOC-CL-0115 |
| 61 | Wt LeuC | L31G/H88A | pOC-CL-0128 |
| 115 | V35G/L411V | L31A/H88S | pOC-CL-0130 |

Alcohol production in engineered MG1655 cells.

MG1655 strains transformed with the pZE_LeuABCD-KA6 and one of the pOC-CL-0### vectors listed in Table 3 were selected on LB agar plates containing 100 ug/mL ampicillin and 25 ug/mL kanamycin. A 50 mL starter culture in LB medium containing 100 ug/mL ampicillin and 25 ug/mL kanamycin was initiated using a single colony from the dual antibiotic LB agar plate and incubated overnight at 37° C. in an incubator shaker set at 200 rpm. After 12-16 hours of incubation, serum bottles containing 5 mL of sterile modified 2×M9 medium (composition shown in Table 4) with 100 ug/mL ampicillin and 25 ug/ml kanamycin were inoculated with 50 uL of starter culture.

TABLE 4

Medium composition used to demonstrate alcohol production from E. coli recombinantly engineered to contain the '+1 pathway' in combination with LeuCD variants.
2X M9 Medium

| | Conc (g/L) |
|---|---|
| $NA_2HPO_4$ | 13.56 |
| $KH_2PO_4$ | 6 |
| $NH_4Cl$ | 2 |
| NaCl | 1 |
| Yeast Extract | 10 |
| Glucose | 40 |
| 92949 Trace Metal Mix A5 w/Co | 1 |

Cultures were incubated at 37° C. with shaking at 200 rpm and induced after 3 hrs using 0.1 mM of IPTG to express all the genes. The culture temperature was reduced to 30° C. after induction. Cultures were harvested 44 hours after induction by transferring them to 4° C. for 20-30 minutes. Serum bottles were then de-capped, and 1 mL of the fermentation broth was quickly poured into a 15 mL conical tube containing 1 mL of a saturated sodium chloride solution and 2 mL of analytical grade toluene. The broth-sodium chloride-toluene mixture was vortexed for 30 seconds and the toluene extract was subjected to alcohol analysis using a GC/FID method described in International Pub. No. WO/2016/094604 A1, which is incorporated herein by reference in its entirety.

Figure 9:
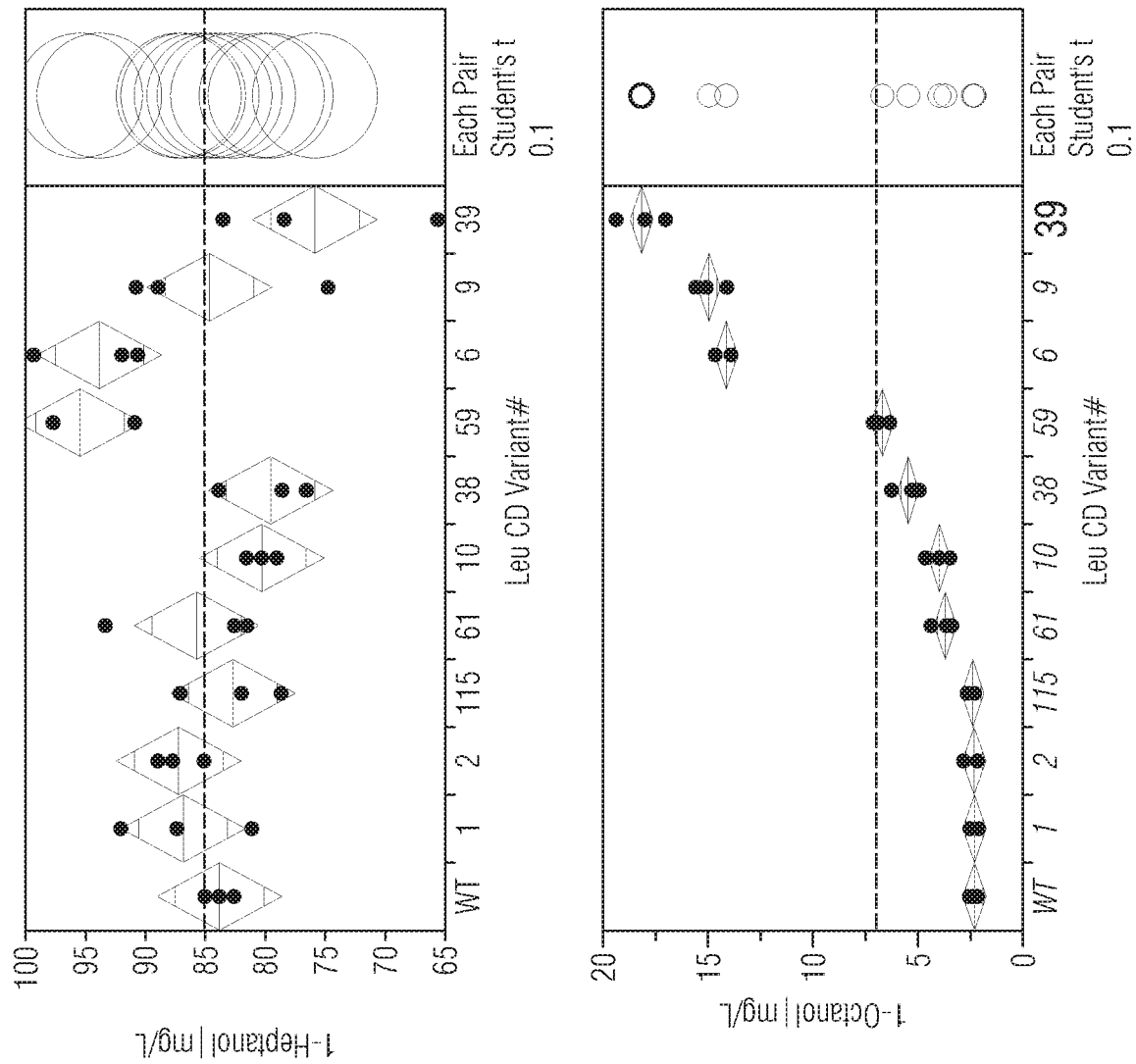
FIG. 9. Statistical analysis of alcohol titers for serum bottle fermentations of *E. coli* containing the '+1 pathway enzymes in combination with the WT and variant LeuCD enzymes.

Table 5 shows the effects of 10 LeuCD variants on the alcohol composition in the strains expressing them along with the other genes mentioned previously. Several of the LeuCD variant expressing cells produced higher amounts of heptanol and/or octanol than the strain expressing only the wild type LeuCD. This suggests that the LeuCD variants reported here are overcoming the barrier towards the production of >C7 alcohols using the non-natural pathway described here. ANOVA analysis of the data shows that LeuCD Variants 6 and 59 increased heptanol titers (FIG. 9, top graph), while Variants 6, 9, 10, 38, 39, and 61 increased octanol titers (FIG. 9, bottom graph) that were significantly higher than those produced by the wild type enzyme. Cells expressing LeuCD Variants 6, 9 or 39 produced >6-fold higher amounts of octanol than the WT LeuCD enzyme (FIG. 9, bottom graph).

circumstances, any of the variants listed in Table 1 (or Table 5) may be suited better even though they may not be having the highest efficiency in isomerizing 2-HM.

The LeuCD' variants were initially screened for activity against a single high concentration of 3-IPM, 2-BM and 3-HM before determining the catalytic efficiency of selected few (Table 1 and Table 2). Without being bound by any theory, the results illustrated in Table 2 may be interpreted as suggesting that replacing Val-35 and/or Leu-411 of LeuC with amino acids having smaller hydrophobic side chains, e.g., valine, alanine for Val-35 and/or valine, alanine, or glycine for Leu-411, and/or Leu-31 and/or His-88 of LeuD with amino acids having smaller hydrophobic side chains, e.g., valine, alanine, or glycine for Leu-31 and/or serine or alanine for His-88, may in some instances simultaneously decrease enzyme activity against 3-IPM, and increase

TABLE 5

The mean alcohol titers for serum bottle fermentations of *E. coli* containing the '+1 pathway' enzymes in combination with the WT and variant LeuCD enzymes.

| Variant # | 1-Butanol | 1-Pentanol | 1-Hexanol | 1-Heptanol | 1-Octanol | Total Alcohols |
|---|---|---|---|---|---|---|
| WT | 238.5 ± 12.0 | 139.1 ± 4.8 | 69.2 ± 1.1 | 83.9 ± 1.2 | 2.3 ± 0.2 | 533.1 ± 18.9 |
| 1 | 242.4 ± 8.1 | 145.0 ± 7.2 | 72.4 ± 4.4 | 87.0 ± 5.4 | 2.4 ± 0.2 | 549.2 ± 25.3 |
| 2 | 242.1 ± 8.5 | 144.9 ± 3.4 | 72.9 ± 1.2 | 87.5 ± 2.0 | 2.4 ± 0.3 | 549.8 ± 14.1 |
| 115 | 248.6 ± 12.0 | 144.0 ± 8.6 | 71.9 ± 3.6 | 82.8 ± 4.3 | 2.6 ± 0.1 | 550.0 ± 28.6 |
| 61 | 252.7 ± 9.8 | 146.1 ± 6.5 | 73.5 ± 3.7 | 85.9 ± 6.5 | 3.9 ± 0.5 | 562.2 ± 26.8 |
| 10 | 257.9 ± 7.6 | 125.6 ± 1.2 | 58.8 ± 0.7 | 80.3 ± 1.3 | 4.1 ± 0.6 | 526.7 ± 9.8 |
| 38 | 275.0 ± 17.2 | 142.7 ± 5.1 | 74.7 ± 1.6 | 79.8 ± 3.8 | 5.6 ± 0.7 | 577.8 ± 27.9 |
| 59 | 302.2 ± 9.4 | 159.2 ± 5.0 | 66.8 ± 2.5 | 95.5 ± 3.9 | 6.8 ± 0.4 | 630.6 ± 17.3 |
| 6 | 289.4 ± 6.0 | 160.3 ± 6.0 | 72.4 ± 3.7 | 93.9 ± 4.7 | 14.2 ± 0.4 | 630.2 ± 19.6 |
| 9 | 310.1 ± 12.6 | 158.8 ± 7.9 | 65.5 ± 4.9 | 84.8 ± 8.7 | 15.0 ± 0.8 | 634.4 ± 34.3 |
| 39 | 292.6 ± 16.2 | 145.9 ± 10.2 | 63.0 ± 7.1 | 76.0 ± 9.2 | 18.2 ± 1.2 | 595.7 ± 42.9 |

*ADH6 and kivD were also included in all strain constructs. All titers are shown in milligrams per liter ± standard deviation across a minimum of triplicate experiments. Titers were measured 44 hours after induction.

Example 6: Results and Discussion

To improve the efficiency of the "+1" pathway in producing 2-ketononanoate, isopropylmalate isomerase would desirably efficiently catalyze isomerization of all the intermediate 2-alkylmalates to their corresponding 3-alkylmalates. The three substrates used for the evaluation of LeuCD variants are representative of these intermediate 2-alkylmalates. More specifically, 2-isopropylmalate (i.e., 2-IPM) is representative of the shorter 2-alkylmalate substrates expected to form during the earlier cycles of the "+1" iterative pathway; 2-butylmalate (i.e., 2-BM) and 2-hexylmalate (i.e., 2-HM) are mid to largest 2-alkylmalates, respectively, formed in the iterative pathway en route to 2-ketononanoate formation. For the optimal efficiency of the "+1" iterative pathway for synthesizing 2-ketononanoate in vitro, the LeuCD complex combination needs to efficiently catalyze the conversion of each intermediate 2-alkylmalate to its corresponding 3-alkylmalate. As evident from Table 2, the efficiency of the wild type LeuCD complex decreases as the size of the alkyl chain increases, with 2-HM being a poor substrate. Under these conditions, addition of Variant 6 to the reaction mixture would improve the efficiency of the pathway in producing 2-ketononanoate.

For the optimal efficiency of the "+1" iterative pathway, for making 2-ketononanoate in vivo the LeuCD complex combination needs to match its efficiency in catalyzing the conversion of each intermediate 2-alkylmalate with the efficiency of other enzymes within the cell and also other competing metabolic pathways within the cell. Under such enzyme activity against 3-HM. As shown in Table 1, various combinations of these variants exhibited higher activity than the wild type enzyme against 3-HM. This analysis suggests that the wild type LeuCD is highly efficient in capturing its native substrate, i.e., 2-IPM, for catalysis, but becomes progressively less active as a catalyst as the "+1" pathway iterates for elongating 2-ketobutyrate to a $C_7$-$C_{11}$ 2-ketoacid, such as, in this instance, 2-ketononanoate. Variants 1 (V35A-LeuC+wt LeuD), 5 (wt-LeuC+L31A LeuD), 6 (wt-LeuC+L31G-LeuD), 9 (V35A-LeuC+L31G-LeuD), 10 (V35A-LeuC+L31V), 18 (L411V-LeuC+L31G-LeuD), 31 (V35A/L411V-LeuC+L31V-LeuD), 32 (V35A/L411V-LeuC+L31A-LeuD), 39 (W35A/L411G-LeuC+L31G-LeuD), 59 (wt-LeuC+L31V/H88A-LeuD), 61 (wt-LeuC+L31G/H88A-LeuD), 64 (wt-LeuC+L31G/H88S-LeuD), and 115 (V35G/L411V-LeuC+L31A/H88S-LeuD) had from 2- to 341-fold higher activity against 2-HM than the wild type LeuCD (Variant 3). While these various substitutions in LeuC and LeuD increased the activity against 2-HM, they diminished or abolished activity against 2-IPM. Together, the data indicate that these would be significantly less effective than the wild type enzyme in the earlier cycles of "+1" pathway during the elongation of 2-ketobutyrate, but will be 2- to 341-fold more efficient during later stages of elongation of 2-ketobutyrate to $C_8$-$C_{11}$ 2-ketoacids. Expressing both the wild type LeuCD and variant 1, 5, 6, 9, 10, 18, 31, 32, 39, 59, 61, 64, or 115 would overcome LeuCD related bottleneck during the elongation of 2-ketobutyrate to $C_7$-$C_{11}$ 2-ketoacid and eventually, $C_6$-$C_{10}$ alcohol.

The data shows that the genetically modified LeuCD' enzyme generally operates at a higher catalytic efficiency than that of the wild type enzyme to catalyze, as shown, 2-hexylmalate to form 3-hexylmalate and subsequently 2-ketononanoate. It can also be inferred that it will more efficiently catalyze 2-pentylmalate to form 3-pentylmalate and subsequently 2-ketooctanoate. Finally, it will also likely carry out combinations of these conversions at a higher catalytic efficiency.

As shown in Table 5, several of the LeuCD variant expressing cells produced higher amounts of heptanol and/or octanol than the strain expressing only the wild type LeuCD. This suggests that the LeuCD variants reported here are overcoming the barrier towards the production of >C7 alcohols using the non-natural pathway used here. LeuCD tag. To the resulting modified gene, additional bases were added to introduce a NcoI and a SacI restriction site at the 5'- and 3'-end, respectively, for cloning purposes. The whole DNA sequence was chemically synthesized and cloned into an E. coli expression vector, pRSFDuet-1 (purchased from EMD Biosciences) at the NcoI and SacI sites by SGI Inc. LeuD was also chemically synthesized (without any tag) and cloned into a pETDuet-1 vector. Fully functional isopropylmalate isomerase was produced in E. coli BL21(DE3) (purchased from EMD Biosciences) cells by cotransfecting them with individual LeuC and LeuD subunit expressing vectors (i.e., the PRSFDuet-1 vector and the pETDuet-1 vector).

TABLE 6

Amino acid sequences of the N-terminus His-tagged LeuC (i.e., N-His LeuC insert 479 aa) and the C-terminus His-tagged LeuC (i.e., C-His LeuC insert 476 aa).

| His-tagged LeuC | SEQ ID No. | Amino Acid Sequence |
| --- | --- | --- |
| N-His LeuC (479 amino acids) | 42 | MGSSHHHHHHSSGMAKTLYEKLFDAHVVYEAENETPLLYIDRHLVHEV TSPQAFDGLRAHGRPVRQPGKTFATMDHNVSTQTKDINACGEMARIQMQ ELIKNCKEFGVELYDLNHPYQGIVHVMGPEQGVTLPGMTIVCGDSHTATH GAFGALAFGIGTSEVEHVLATQTLKQGRAKTMKIEVQGKAAPGITAKDIV LAIIGKTGSAGGTGHVVEFCGEAIRDLSMEGRMTLCNMAIEMGAKAGLV APDETTFNYVKGRLHAPKGKDFDDAVAYWKTLQTDEGATFDTVVTLQA EEISPQVTWGTNPGQVSVNDNIPDPASFADPVERASAEKALAYMGLKPGI PLTEVAIDKVFIGSCTNSRIEDLRAAAEIAKGRKVAPGVQALVVPGSGPVK AQAEAEGLDKIFIEAGFEWRLPGCSMCLAMNNDRLNPGERCASTSNRNFE GRQGRGGRTHLVSPAMAAAAAVTGHFADIRNIK |
| C-His LeuC (476 amino acids) | 41 | MAKTLYEKLFDAHVVYEAENETPLLYIDRHLVHEVTSPQAFDGLRAHGRP VRQPGKTFATMDHNVSTQTKDINACGEMARIQMQELIKNCKEFGVELYD LNHPYQGIVHVMGPEQGVTLPGMTIVCGDSHTATHGAFGALAFGIGTSEV EHVLATQTLKQGRAKTMKIEVQGKAAPGITAKDIVLAIIGKTGSAGGTGH VVEFCGEAIRDLSMEGRMTLCNMAIEMGAKAGLVAPDETTFNYVKGRLH APKGKDFDDAVAYWKTLQTDEGATFDTVVTLQAEEISPQVTWGTNPGQV ISVNDNIPDPASFADPVERASAEKALAYMGLKPGIPLTEVAIDKVFIGSCTN SRIEDLRAAAEIAKGRKVAPGVQALVVPGSGPVKAQAEAEGLDKIFIEAGF EWRLPGCSMCLAMNNDRLNPGERCASTSNRNFEGRQGRGGRTHLVSPAM AAAAAVTGHFADIRNIKSSHHHHHHSS | variants 6 and 59 increased heptanol titers, while variants 6, 9, 10, 38, 39, 59, and 61 increased octanol titers compared to those produced by the wild type enzyme. Cells expressing LeuCD variants 6, 9 or 39 produced >6-fold higher amounts of octanol than the WT LeuCD enzyme.

Example 7: Preparing Genetically Modified LeuCD Enzyme Complexes Expressing LeuC Having an N-Terminus (his)$_6$-Tag or LeuC Having a C-Terminus (his)$_6$-Tag Genetically modified LeuCD enzyme complexes expressing LeuC having an N-terminus (His)$_6$-tag or LeuC having a C-terminus (His)$_6$-tag were prepared. Specifically, the gene sequences of LeuC (EcoGene Accession No. EG11576) and LeuD (EcoGene Accession No. EG11575) were downloaded from the E. Coli genome website, EcoGene (http://ecogene.org). Codons of 13 additional amino acids that included six histidines were fused upstream of the codon of Met-1 of the LeuC gene sequence. Such a modification allowed expression of a (His)$_6$-tagged LeuC having 13 additional amino acids on the N-terminus. The resulting 479 amino acid sequence of the His-tagged LeuC having 13 additional amino acids on the N-terminus is provided in Table 6. The 13 amino acids underlined in Table 6 are the 13 amino acids added to the N-terminus including the (His)$_6$-

Codons of 10 additional amino acids that included six histidines were also separately fused downstream of the codon of Lys-466 of the LeuC gene sequence. Such a modification allowed expression of a (His)$_6$-tagged LeuC having 10 additional amino acids on the C-terminus. The resulting 476 amino acid sequence of the (His)$_6$-tagged LeuC having 10 additional amino acids on the C-terminus is provided in Table 6. The 10 amino acids underlined in Table 6 are the 10 amino acids added to the C-terminus including the (His)$_6$-tag. To the resulting modified gene, additional bases were added to introduce a NcoI and a SacI restriction site at the 5'- and 3'-end, respectively, for cloning purposes. The whole DNA sequence was chemically synthesized and cloned into an E. coli expression vector, pRSFDuet-1 (purchased from EMD Biosciences) at the NcoI and SacI sites by SGI Inc. LeuD was also chemically synthesized (without any tag) and cloned into a pETDuet-1 vector. Fully functional isopropylmalate isomerase was produced in E. coli BL21(DE3) (purchased from EMD Biosciences) cells by cotransfecting them with individual LeuC and LeuD subunit expressing vectors (i.e., the PRSFDuet-1 vector and the pETDuet-1 vector).

Cotransfection of the E. coli BL21(DE3) cells with the N-His LeuC, C-His LeuC, and/or LeuD expression vectors was performed using standard techniques. Cells harboring the expression vectors were selected on LB agar plates containing 100 μg/mL of ampicillin and 50 μg/mL of kanamycin. A starter culture was started by transferring a single colony of transformant into 50 mL of LB medium containing 100 μg/mL of ampicillin and 50 μg/mL of kanamycin and incubated at 37° C. with shaking at 220 rpm overnight. The next day, 7 mL of starter culture was inoculated into 800 mL of Terrific Broth (i.e., TB) and the culture was incubated at 37° C. until it reached an $OD_{600}$ nm of 0.5. Isopropyl β-D-1-thiogalacto-pyranoside (i.e., IPTG) at a final concentration of 1 mM was added to induce the expression of the LeuCD complex or its variant and the culture was transferred to a 15° C. incubator for 16 hours (h). At the end of 16 h, the culture was centrifuged at 8000 revolutions per minute (rpm) to pelletize the cells. The cell pellet was divided into four aliquots and stored at −80° C. until disruption for the isolation of the LeuCD complex.

The LeuCD complex was isolated from the cell pellet in an anaerobic chamber (acquired from COY Lab Products (MI, USA)) maintained under 98% nitrogen and 2% Hydrogen. The *E. coli* pellet prepared was suspended in 50 mM HEPES buffer (pH 8.0) containing 0.2 mM ferrous ammonium sulfate, 10 mM DTT, 30 mM KCl, 5 mM $MgCl_2$ and protease inhibitor cocktail (acquired from SIGMA-ALDRICH, USA). To the cells, 2.5 gm of 0.1 mm glass beads were added and the cells were disrupted on a Geno grinder for 3 minutes at 1750 rpm. Cell debris and the glass beads were pelleted by centrifugation and the supernatant was mixed with equal volume of 50% glycerol and stored anaerobically at −20° C.

Example 8: Evaluation of Substrate Specificity of Genetically Modified LeuCD Enzyme Complexes Expressing LeuC Having an N-Terminus (his) 6-Tag or LeuC Having a C-Terminus (his) 6-Tag The high-throughput (i.e., HTP) LeuCD enzyme assay described in Example 3 was used for evaluating the substrate specificity of genetically modified LeuCD enzyme complexes, containing LeuC having either an N-terminus (His)$_6$-tag or a C-terminus (His)$_6$-tag, as prepared in Example 7. The activity of the genetically modified LeuCD enzyme complexes against 2-IPM and 2-HM were evaluated as described in Example 3. As described in Example 3, the assay involved coupling the LeuCD reaction with that of the LeuB reaction. Thus, during the assay, 2-IPM was initially isomerized to 3-isopropylmalate (3-IPM) by LeuCD which was immediately converted to 2-ketoisocaproate by the LeuB enzyme present in the assay mixture. Likewise, in the assays involving 2-HM as a substrate, the end product formed in the assay was 2-ketononanoate. The activity of LeuCD variant was calculated from the amounts of respective 2-ketoacids produced in the coupled assay.

Briefly, the assay involved incubating the whole cell lysate from cells expressing the modified LeuCD enzyme complexes of Example 7 with 2 mM 2-IPM or 2-HM in a mixture containing: 20 μg of wild type LeuB, 16 μg of a L96G/V198A variant of LeuB, 5 mM $NAD^+$, 10 mM DTT, 20 μg bovine serum albumin, 30 mM KCl, 5 mM $MgCl_2$, and 50 mM HEPES pH 8. The total assay volume was 100 μL and was performed anaerobically in a COY chamber at room temperature for a period of 1 hr. The reaction was stopped by the addition of an equal volume of a mixture containing 20% formic acid and 10% methanol. The 2-ketoacids formed in the coupled assay were quantitated using an Agilent 1290 Infinity uHPLC coupled with an AB Sciex 5500 QTrap mass spectrometer. Following the separation of the 2-ketoacids on Waters Acquity HSS T3 1.8 μM 3.0×150 mm reverse phase column under reverse phase conditions, the detection and quantitation was performed in the mass spectrometer by single quadrupole select ion monitoring method that operated in negative mode. Quantitation was based off an external calibration curve generated for each 2-ketoacid from custom synthesized analytical grade standard reference material with the exception of 4-methyl-2-oxovalerate which was commercially available from Sigma-Aldrich.

The activity of each genetically modified LeuCD enzyme complex against 2-IPM and 2-HM was compared. 2-IPM is the native substrate of LeuCD and activity against it would indicate that the engineered enzymes would be able to catalyze the earlier cycles of "+1" pathway during 2-ketobutyrate elongation to 2-Ketononanoate (i.e., 2-KN). 2-HM is a non-native substrate of LeuCD. LeuCD variants having higher activity against 2-HM than the wild type LeuCD would be capable of improving 2-KN yield by making the later cycles of "+1" pathway during 2-ketobutyrate elongation more efficient. The HTP assay involved coupling of the LeuCD activity with that of the next enzyme in the "+1" LeuABCD pathway, isopropylmalate dehydrogenase (i.e., LeuB). Thus, 3-isopropylmalate (i.e., 3-IPM) or 3-hexylmalate (i.e., 3-HM) produced from 2-IPM or 2-HM, respectively, by LeuCD were oxidatively decarboxylated by LeuB to 2-ketoisocaproate and 2-ketononanoate (i.e., 2-KN). All the 2-ketoacids were then quantitated using LC/MS.

Figure 10A:
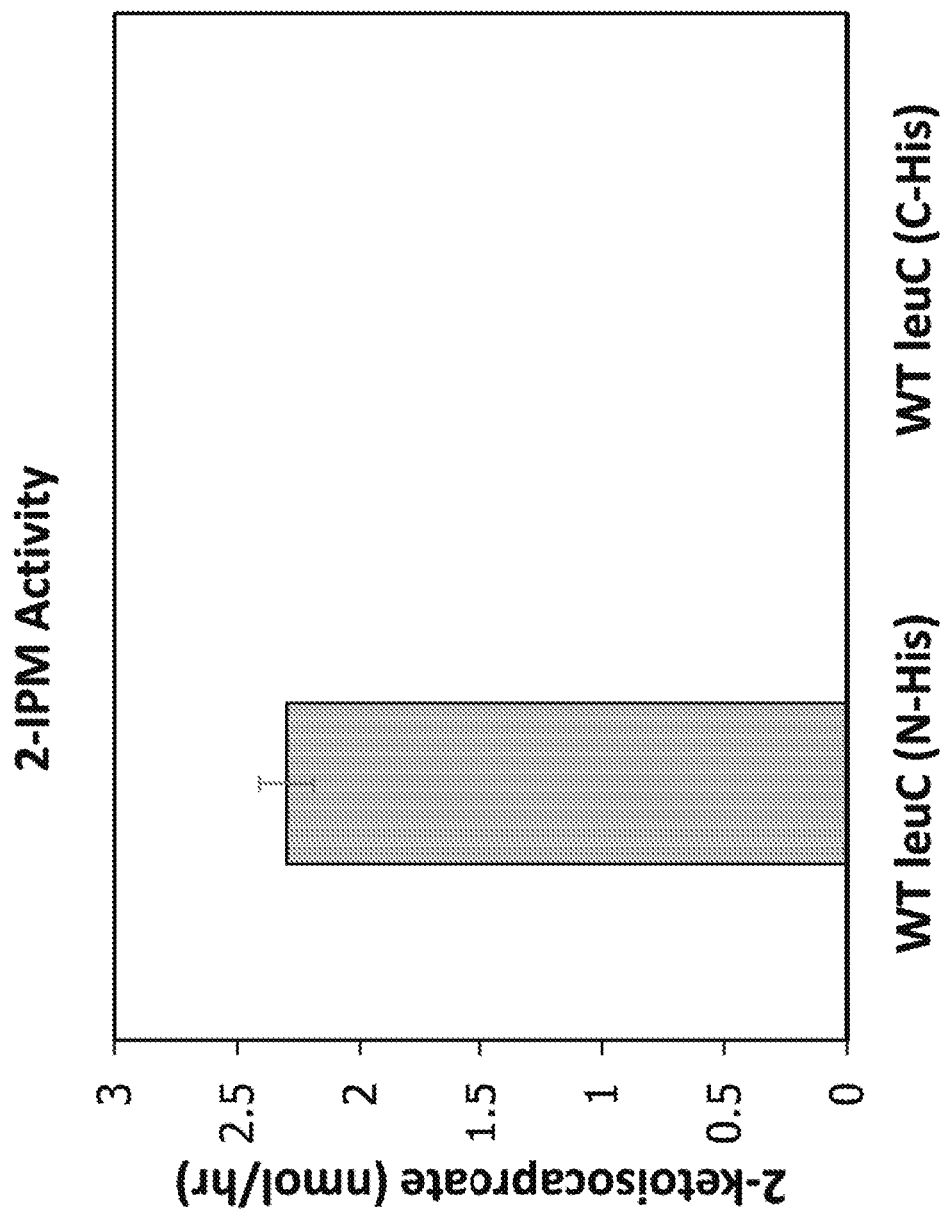
FIG. 10A. Activity of variant LeuCD enzymes for 2-isopropylmalate.
Figure 10B:
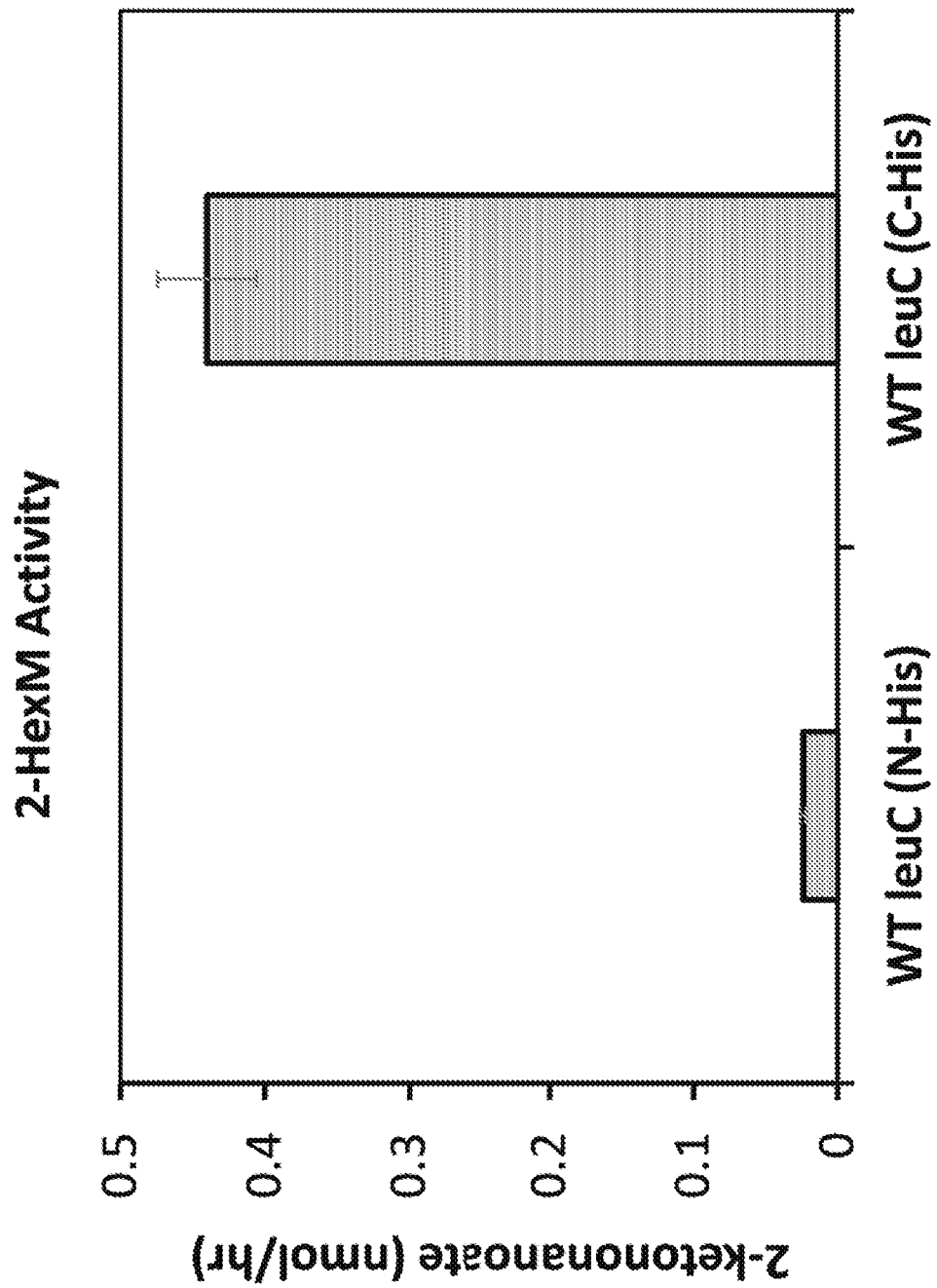
FIG. 10B. Activity of variant LeuCD enzymes for 2-hexylmalate.

As shown in FIGS. 10A-10B, the genetically modified LeuCD enzyme complex expressing LeuC having an N-terminus (His)$_6$-tag (i.e., N-His LeuC; Table 6) exhibited 100-fold higher activity against 2-IPM (FIG. 10A) as compared to 2-HM (FIG. 10B). Interestingly, while genetically modified LeuCD enzyme complex expressing LeuC having a C-terminus (His)$_6$-tag (i.e., C-His LeuC; Table 6) exhibited virtually no detectable activity against 2-IPM (FIG. 10A), C-His LeuC exhibited significantly higher activity against 2-HM (FIG. 10B). Without being bound by the theory, it is believed that the additional amino acid sequence on the C-terminus of LeuC widened the active site of LeuCD such that LeuCD could no longer accept 2-IPM as a substrate; rather, C-His LeuC preferred the larger compound of 2-HM as its substrate. Thus, it is believed that the addition of such an amino acid sequence on the C-terminus of LeuC would improve the elongation of 2-ketobutyrate to $C_7$-$C_{11}$ 2-ketoacids, and eventually, $C_6$-$C_{10}$ alcohols, in the "+1" pathway.

DEPOSIT INFORMATION

Microbial strains of *E. coli* containing the LeuCD variants 38 (V35A/L411G-LeuC+L31A-LeuD), *E. coli* containing the LeuCD variant 39 (W35A/L411G-LeuC+L31G-LeuD), *E. coli* containing the LeuCD variant 10 (V35A-LeuC+L31V-LeuD), *E. coli* containing the LeuCD variant 6 (wt-LeuC+L31G-LeuD), *E. coli* containing the LeuCD variant 59 (wt-LeuC+L31V/H88A-LeuD), *E. coli* containing the LeuCD variant 9 (V35A-LeuC+L31G-LeuD), and *E. coli* containing the LeuCD variant 61 (wt-LeuC+L31G/H88A-LeuD), disclosed previously, have been made with the American Type Culture Collection (ATCC), 10801 University Boulevard, Manassas, Va. 20110, under the provisions of the Budapest Treaty on the International Recognition of the Deposit of Microorganisms for the Purpose of Patent Procedures. The date of deposit was Sep. 2, 2016 on behalf of Dow Global Technologies. The deposit of 25 vials of each strain were taken from the same deposits maintained by the inventors since prior to the filing date of this application. The deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced as necessary during that period. Microbial strain of *E. coli* containing the LeuCD variant 38 (V35A/L411G-LeuC+L31A-LeuD) was deposited on Sep. 2, 2016 at the ATCC (ATCC Patent Deposit Designation: PTA-123472). Microbial strain of *E. coli* containing the LeuCD variant 39 (W35A/L411G-LeuC+L31G-LeuD) was deposited on Sep. 2, 2016 at the ATCC (ATCC Patent Deposit Designation: PTA-123473). Microbial strain of *E. coli* containing the LeuCD variant 10 (V35A-LeuC+L31V-LeuD) was deposited on Sep. 6, 2016 at the ATCC (ATCC Patent Deposit Designation: PTA-123474). Microbial strain of *E. coli* containing the LeuCD variant 6 (wt-LeuC+L31G-LeuD) was deposited on Sep. 6, 2016 at the ATCC (ATCC Patent Deposit Designation: PTA-123475). Microbial strain of *E. coli* containing the LeuCD variant 59 (wt-LeuC+L31V/H88A-LeuD) was deposited on Sep. 6, 2016 at the ATCC (ATCC Patent Deposit Designation: PTA-123477). Microbial strain of *E. coli* containing the LeuCD variant 9 (V35A-LeuC+L31G-LeuD) was deposited on Sep. 6, 2016 at the ATCC (ATCC Patent Deposit Designation: PTA-123478). Microbial strain of *E. coli* containing the LeuCD variant 61 (wt-LeuC+L31G/H88A-LeuD) was deposited on Sep. 6, 2016 at the ATCC (ATCC Patent Deposit Designation: PTA-123479).

The invention claimed is:

1. A microbial organism comprising at least one genetically modified LeuCD' enzyme complex comprising:
   (a) a genetically modified LeuC' subunit comprising:
       (1) an amino acid sequence with at least 95% homology to SEQ ID NO: 1 having a C-terminus; and
       (2) a C-terminal amino acid or peptide coupled to the C-terminus of the amino acid sequence of (a)(1), wherein the C-terminal amino acid is chosen from any naturally occurring amino acid, and wherein the C-terminal peptide comprises an amino acid sequence: $(Xaa)_1(Xaa)_2(Xaa)_3(Xaa)_4(Xaa)_5(Xaa)_6(Xaa)_7(Xaa)_8(Xaa)_9(Xaa)_{10}$ (SEQ ID NO: 39) in which:
       $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, and $(Xaa)_{10}$ are each independently chosen from any naturally occurring amino acid, or are absent, provided that at least two of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present in the C-terminal peptide; and
   (b) a LeuD subunit comprising an amino acid sequence with at least 90% homology to SEQ ID NO: 2, wherein the at least one genetically modified LeuCD' enzyme complex has activity against 2-hexylmalate (2-HM).

2. The microbial organism according to claim 1, wherein the genetically modified LeuC' subunit comprises the C-terminal peptide, and wherein at least six of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ are present.

3. The microbial organism according to claim 1, wherein the genetically modified LeuC' subunit comprises the C-terminal peptide, and wherein each of $(Xaa)_1$, $(Xaa)_2$, $(Xaa)_3$, $(Xaa)_4$, $(Xaa)_5$, $(Xaa)_6$, $(Xaa)_7$, $(Xaa)_8$, $(Xaa)_9$, or $(Xaa)_{10}$ present in the C-terminal peptide is independently chosen from Ser, Thr, His, Lys, and Arg.

4. The microbial organism according to claim 1, wherein:
   the genetically modified LeuC' subunit comprises the C-terminal peptide;
   $(Xaa)_1$, $(Xaa)_2$, $(Xaa)_9$, and $(Xaa)_{10}$ are each independently chosen from Ser and Thr; and
   $(Xaa)_3$, $(Xaa)_4$, $(Xaa)_5$, $(Xaa)_6$, $(Xaa)_7$, and $(Xaa)_8$ are each independently chosen from His, Lys, and Arg.

5. The microbial organism according to claim 1, wherein the genetically modified LeuC' subunit comprises the C-terminal peptide (SEQ ID NO: 40).

6. The microbial organism according to claim 1, wherein the LeuD subunit consists of the amino acid sequence with at least 90% homology to SEQ ID NO: 2.

7. The microbial organism according to claim 1, wherein the valine at position 35 of SEQ ID NO: 1 is substituted with alanine or glycine.

8. The microbial organism according to claim 1, wherein the leucine at position 411 of SEQ ID NO: 1 is substituted with valine, alanine, or glycine.

9. The microbial organism according to claim 1, wherein the leucine at position 31 of SEQ ID NO: 2 is substituted with valine, alanine, or glycine.

10. The microbial organism according to claim 1, wherein the histidine at position 88 of SEQ ID NO: 2 is substituted with alanine or serine.

* * * * *

SEQUENCE LISTING

```
<160> NUMBER OF SEQ ID NOS: 42

<210> SEQ ID NO 1
<211> LENGTH: 466
<212> TYPE: PRT
<213> ORGANISM: Escherichia coli

<400> SEQUENCE: 1

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270
```

```
Phe Asp Thr Val Val Thr Leu Gln Ala Glu Glu Ile Ser Pro Gln Val
            275                 280                 285

Thr Trp Gly Thr Asn Pro Gly Gln Val Ile Ser Val Asn Asp Asn Ile
        290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Glu Ile Ala Lys Gly Arg Lys Val Ala
            355                 360                 365

Pro Gly Val Gln Ala Leu Val Val Pro Gly Ser Gly Pro Val Lys Ala
        370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
450                 455                 460

Ile Lys
465

<210> SEQ ID NO 2
<211> LENGTH: 201
<212> TYPE: PRT
<213> ORGANISM: Escherichia coli

<400> SEQUENCE: 2

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
                20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
        50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175
```

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 3
<211> LENGTH: 466
<212> TYPE: PRT
<213> ORGANISM: Artificial Sequence
<220> FEATURE:
<223> OTHER INFORMATION: Synthesized - Modified LeuC (V35A)

<400> SEQUENCE: 3

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Ala Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

-continued

```
Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
        370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Arg Thr His Leu Val Ser Pro Ala
            435                 440                 445

Met Ala Ala Ala Ala Val Thr Gly His Phe Ala Asp Ile Arg Asn
    450                 455                 460

Ile Lys
465

<210> SEQ ID NO 4
<211> LENGTH: 466
<212> TYPE: PRT
<213> ORGANISM: Artificial Sequence
<220> FEATURE:
<223> OTHER INFORMATION: Synthesized - Modified LeuC (V35G)

<400> SEQUENCE: 4

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Gly Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220
```

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
            245                 250                 255

Asp Ala Val Ala Tyr Trp Lys Thr Leu Gln Thr Asp Glu Gly Ala Thr
        260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
                340                 345                 350

Glu Asp Leu Arg Ala Ala Ala Glu Ile Ala Lys Gly Arg Lys Val Ala
            355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Leu Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 5
<211> LENGTH: 466
<212> TYPE: PRT
<213> ORGANISM: Artificial Sequence
<220> FEATURE:
<223> OTHER INFORMATION: Synthezied - Modified LeuC (L411A)

<400> SEQUENCE: 5

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

```
Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
                180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
        210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
                260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
        290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
                340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
        370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Ala Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 6
<211> LENGTH: 466
<212> TYPE: PRT
<213> ORGANISM: Artificial Sequence
<220> FEATURE:
<223> OTHER INFORMATION: Synthesized - Modified LeuC (L411G)

<400> SEQUENCE: 6
```

-continued

```
Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415
```

```
Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
    450                 455                 460

Ile Lys
465

<210> SEQ ID NO 7
<211> LENGTH: 466
<212> TYPE: PRT
<213> ORGANISM: Artificial Sequence
<220> FEATURE:
<223> OTHER INFORMATION: Synthesized - Modified LeuC (L411V)

<400> SEQUENCE: 7

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300
```

```
Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
                340                 345                 350

Glu Asp Leu Arg Ala Ala Glu Ile Ala Lys Gly Arg Lys Val Ala
                355                 360                 365

Pro Gly Val Gln Ala Leu Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Val Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Gly Arg Thr His Leu Val Ser Pro Ala
                435                 440                 445

Met Ala Ala Ala Ala Val Thr Gly His Phe Ala Asp Ile Arg Asn
450                 455                 460

Ile Lys
465

<210> SEQ ID NO 8
<211> LENGTH: 466
<212> TYPE: PRT
<213> ORGANISM: Artificial Sequence
<220> FEATURE:
<223> OTHER INFORMATION: Synthesized - Modified LeuC (V35A L411A)

<400> SEQUENCE: 8

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Ala Thr Ser Pro Gln Ala Phe Asp Gly Leu Arg Ala His Gly
                35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
                100                 105                 110

Pro Glu Gln Gly Val Thr Leu Pro Gly Met Thr Ile Val Cys Gly Asp
                115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
                180                 185                 190
```

Ser Ala Gly Gly Thr Gly His Val Glu Phe Cys Gly Glu Ala Ile
195 200 205

Arg Asp Leu Ser Met Glu Gly Arg Met Thr Leu Cys Asn Met Ala Ile
210 215 220

Glu Met Gly Ala Lys Ala Gly Leu Val Ala Pro Asp Glu Thr Thr Phe
225 230 235 240

Asn Tyr Val Lys Gly Arg Leu His Ala Pro Lys Gly Lys Asp Phe Asp
245 250 255

Asp Ala Val Ala Tyr Trp Lys Thr Leu Gln Thr Asp Glu Gly Ala Thr
260 265 270

Phe Asp Thr Val Val Thr Leu Gln Ala Glu Glu Ile Ser Pro Gln Val
275 280 285

Thr Trp Gly Thr Asn Pro Gly Gln Val Ile Ser Val Asn Asp Asn Ile
290 295 300

Pro Asp Pro Ala Ser Phe Ala Asp Pro Val Glu Arg Ala Ser Ala Glu
305 310 315 320

Lys Ala Leu Ala Tyr Met Gly Leu Lys Pro Gly Ile Pro Leu Thr Glu
325 330 335

Val Ala Ile Asp Lys Val Phe Ile Gly Ser Cys Thr Asn Ser Arg Ile
340 345 350

Glu Asp Leu Arg Ala Ala Ala Glu Ile Ala Lys Gly Arg Lys Val Ala
355 360 365

Pro Gly Val Gln Ala Leu Val Val Pro Gly Ser Gly Pro Val Lys Ala
370 375 380

Gln Ala Glu Ala Glu Gly Leu Asp Lys Ile Phe Ile Glu Ala Gly Phe
385 390 395 400

Glu Trp Arg Leu Pro Gly Cys Ser Met Cys Ala Ala Met Asn Asn Asp
405 410 415

Arg Leu Asn Pro Gly Glu Arg Cys Ala Ser Thr Ser Asn Arg Asn Phe
420 425 430

Glu Gly Arg Gln Gly Arg Gly Gly Arg Thr His Leu Val Ser Pro Ala
435 440 445

Met Ala Ala Ala Ala Val Thr Gly His Phe Ala Asp Ile Arg Asn
450 455 460

Ile Lys
465

<210> SEQ ID NO 9
<211> LENGTH: 466
<212> TYPE: PRT
<213> ORGANISM: Artificial Sequence
<220> FEATURE:
<223> OTHER INFORMATION: Synthesized - Modified LeuC (V35A L411G)

<400> SEQUENCE: 9

Met Ala Lys Thr Leu Tyr Glu Lys Leu Phe Asp Ala His Val Val Tyr
1 5 10 15

Glu Ala Glu Asn Glu Thr Pro Leu Leu Tyr Ile Asp Arg His Leu Val
20 25 30

His Glu Ala Thr Ser Pro Gln Ala Phe Asp Gly Leu Arg Ala His Gly
35 40 45

Arg Pro Val Arg Gln Pro Gly Lys Thr Phe Ala Thr Met Asp His Asn
50 55 60

Val Ser Thr Gln Thr Lys Asp Ile Asn Ala Cys Gly Glu Met Ala Arg
65 70 75 80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Gly Arg Thr His Leu Val Ser Pro Ala
        435                 440                 445

Met Ala Ala Ala Ala Val Thr Gly His Phe Ala Asp Ile Arg Asn
450                 455                 460

Ile Lys
465

<210> SEQ ID NO 10
<211> LENGTH: 466
<212> TYPE: PRT

<213> ORGANISM: Artificial Sequence
<220> FEATURE:
<223> OTHER INFORMATION: Synthesized - Modified LeuC (V35A L411V)

<400> SEQUENCE: 10

```
Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Ala Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
```

```
385                 390                 395                 400
Glu Trp Arg Leu Pro Gly Cys Ser Met Cys Val Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Arg Thr His Leu Val Ser Pro Ala
                435                 440                 445

Met Ala Ala Ala Ala Val Thr Gly His Phe Ala Asp Ile Arg Asn
    450                 455                 460

Ile Lys
465

<210> SEQ ID NO 11
<211> LENGTH: 466
<212> TYPE: PRT
<213> ORGANISM: Artificial Sequence
<220> FEATURE:
<223> OTHER INFORMATION: Synthesized - Modified LeuC (V35G L411A)

<400> SEQUENCE: 11

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Gly Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
```

```
                275                 280                 285
Thr Trp Gly Thr Asn Pro Gly Gln Val Ile Ser Val Asn Asp Asn Ile
    290                 295                 300
Pro Asp Pro Ala Ser Phe Ala Asp Pro Val Glu Arg Ala Ser Ala Glu
305                 310                 315                 320
Lys Ala Leu Ala Tyr Met Gly Leu Lys Pro Gly Ile Pro Leu Thr Glu
                325                 330                 335
Val Ala Ile Asp Lys Val Phe Ile Gly Ser Cys Thr Asn Ser Arg Ile
                340                 345                 350
Glu Asp Leu Arg Ala Ala Glu Ile Ala Lys Gly Arg Lys Val Ala
            355                 360                 365
Pro Gly Val Gln Ala Leu Val Val Pro Gly Ser Gly Pro Val Lys Ala
    370                 375                 380
Gln Ala Glu Ala Glu Gly Leu Asp Lys Ile Phe Ile Glu Ala Gly Phe
385                 390                 395                 400
Glu Trp Arg Leu Pro Gly Cys Ser Met Cys Ala Ala Met Asn Asn Asp
                405                 410                 415
Arg Leu Asn Pro Gly Glu Arg Cys Ala Ser Thr Ser Asn Arg Asn Phe
                420                 425                 430
Glu Gly Arg Gln Gly Arg Gly Arg Thr His Leu Val Ser Pro Ala
            435                 440                 445
Met Ala Ala Ala Ala Val Thr Gly His Phe Ala Asp Ile Arg Asn
450                 455                 460
Ile Lys
465

<210> SEQ ID NO 12
<211> LENGTH: 466
<212> TYPE: PRT
<213> ORGANISM: Artificial Sequence
<220> FEATURE:
<223> OTHER INFORMATION: Synthesized - Modified LeuC (V35G L411G)

<400> SEQUENCE: 12

Met Ala Lys Thr Leu Tyr Glu Lys Leu Phe Asp Ala His Val Val Tyr
1               5                   10                  15
Glu Ala Glu Asn Glu Thr Pro Leu Leu Tyr Ile Asp Arg His Leu Val
                20                  25                  30
His Glu Gly Thr Ser Pro Gln Ala Phe Asp Gly Leu Arg Ala His Gly
            35                  40                  45
Arg Pro Val Arg Gln Pro Gly Lys Thr Phe Ala Thr Met Asp His Asn
    50                  55                  60
Val Ser Thr Gln Thr Lys Asp Ile Asn Ala Cys Gly Glu Met Ala Arg
65                  70                  75                  80
Ile Gln Met Gln Glu Leu Ile Lys Asn Cys Lys Glu Phe Gly Val Glu
                85                  90                  95
Leu Tyr Asp Leu Asn His Pro Tyr Gln Gly Ile Val His Val Met Gly
                100                 105                 110
Pro Glu Gln Gly Val Thr Leu Pro Gly Met Thr Ile Val Cys Gly Asp
            115                 120                 125
Ser His Thr Ala Thr His Gly Ala Phe Gly Ala Leu Ala Phe Gly Ile
    130                 135                 140
Gly Thr Ser Glu Val Glu His Val Leu Ala Thr Gln Thr Leu Lys Gln
145                 150                 155                 160
Gly Arg Ala Lys Thr Met Lys Ile Glu Val Gln Gly Lys Ala Ala Pro
```

```
                    165                 170                 175
Gly Ile Thr Ala Lys Asp Ile Val Leu Ala Ile Ile Gly Lys Thr Gly
                180                 185                 190

Ser Ala Gly Gly Thr Gly His Val Val Glu Phe Cys Gly Glu Ala Ile
            195                 200                 205

Arg Asp Leu Ser Met Glu Gly Arg Met Thr Leu Cys Asn Met Ala Ile
        210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Gly Ala Met Asn Asn Asp
                405                 410                 415

Arg Leu Asn Pro Gly Glu Arg Cys Ala Ser Thr Ser Asn Arg Asn Phe
            420                 425                 430

Glu Gly Arg Gln Gly Arg Gly Arg Thr His Leu Val Ser Pro Ala
        435                 440                 445

Met Ala Ala Ala Ala Val Thr Gly His Phe Ala Asp Ile Arg Asn
            450                 455                 460

Ile Lys
465

<210> SEQ ID NO 13
<211> LENGTH: 466
<212> TYPE: PRT
<213> ORGANISM: Artificial Sequence
<220> FEATURE:
<223> OTHER INFORMATION: Synthesized - Modified LeuC (V35G L411V)

<400> SEQUENCE: 13

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Gly Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
```

```
            50                  55                  60
Val Ser Thr Gln Thr Lys Asp Ile Asn Ala Cys Gly Glu Met Ala Arg
 65                  70                  75                  80

Ile Gln Met Gln Glu Leu Ile Lys Asn Cys Lys Glu Phe Gly Val Glu
                     85                  90                  95

Leu Tyr Asp Leu Asn His Pro Tyr Gln Gly Ile Val His Val Met Gly
                100                 105                 110

Pro Glu Gln Gly Val Thr Leu Pro Gly Met Thr Ile Val Cys Gly Asp
                115                 120                 125

Ser His Thr Ala Thr His Gly Ala Phe Gly Ala Leu Ala Phe Gly Ile
                130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Gly Lys Thr Gly
                180                 185                 190

Ser Ala Gly Gly Thr Gly His Val Val Glu Phe Cys Gly Glu Ala Ile
                195                 200                 205

Arg Asp Leu Ser Met Glu Gly Arg Met Thr Leu Cys Asn Met Ala Ile
                210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
                260                 265                 270

Phe Asp Thr Val Val Thr Leu Gln Ala Glu Glu Ile Ser Pro Gln Val
                275                 280                 285

Thr Trp Gly Thr Asn Pro Gly Gln Val Ile Ser Val Asn Asp Asn Ile
                290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
                340                 345                 350

Glu Asp Leu Arg Ala Ala Ala Glu Ile Ala Lys Gly Arg Lys Val Ala
                355                 360                 365

Pro Gly Val Gln Ala Leu Val Val Pro Gly Ser Gly Pro Val Lys Ala
                370                 375                 380

Gln Ala Glu Ala Glu Gly Leu Asp Lys Ile Phe Ile Glu Ala Gly Phe
385                 390                 395                 400

Glu Trp Arg Leu Pro Gly Cys Ser Met Cys Val Ala Met Asn Asn Asp
                405                 410                 415

Arg Leu Asn Pro Gly Glu Arg Cys Ala Ser Thr Ser Asn Arg Asn Phe
                420                 425                 430

Glu Gly Arg Gln Gly Arg Gly Arg Thr His Leu Val Ser Pro Ala
                435                 440                 445

Met Ala Ala Ala Ala Val Thr Gly His Phe Ala Asp Ile Arg Asn
                450                 455                 460

Ile Lys
465
```

<210> SEQ ID NO 14
<211> LENGTH: 201
<212> TYPE: PRT
<213> ORGANISM: Artificial Sequence
<220> FEATURE:
<223> OTHER INFORMATION: Synthesized - Modified LeuD (H88A)

<400> SEQUENCE: 14

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 15
<211> LENGTH: 201
<212> TYPE: PRT
<213> ORGANISM: Artificial Sequence
<220> FEATURE:
<223> OTHER INFORMATION: Synthesized - Modified LeuD (H88G)

<400> SEQUENCE: 15

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly

```
            100                 105                 110
Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 16
<211> LENGTH: 201
<212> TYPE: PRT
<213> ORGANISM: Artificial Sequence
<220> FEATURE:
<223> OTHER INFORMATION: Synthesized - Modified LeuD (H88V)

<400> SEQUENCE: 16

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
                20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 17
<211> LENGTH: 201
<212> TYPE: PRT
<213> ORGANISM: Artificial Sequence
<220> FEATURE:
<223> OTHER INFORMATION: Synthesized - Modified LeuD (H88S)

<400> SEQUENCE: 17
```

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
            130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
                180                 185                 190

Glu Ala Lys Gln Pro Ala Phe Met Asn
            195                 200

<210> SEQ ID NO 18
<211> LENGTH: 201
<212> TYPE: PRT
<213> ORGANISM: Artificial Sequence
<220> FEATURE:
<223> OTHER INFORMATION: Synthesized - Modified LeuD (L31A)

<400> SEQUENCE: 18

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
            130                 135                 140

Asp Val Asp Leu Glu Ala Gln Glu Val Lys Ala Gly Glu Lys Thr Tyr
145                 150                 155                 160

```
Arg Phe Thr Ile Asp Ala Phe Arg Arg His Cys Met Met Asn Gly Leu
            165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 19
<211> LENGTH: 201
<212> TYPE: PRT
<213> ORGANISM: Artificial Sequence
<220> FEATURE:
<223> OTHER INFORMATION: Synthesized - Modified LeuD (L31A H88A)

<400> SEQUENCE: 19

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
            165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 20
<211> LENGTH: 201
<212> TYPE: PRT
<213> ORGANISM: Artificial Sequence
<220> FEATURE:
<223> OTHER INFORMATION: Synthesized - Modified LeuD (L31A H88G)

<400> SEQUENCE: 20

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60
```

Phe Pro Gln Tyr Gln Gly Ala Ser Ile Leu Leu Ala Arg Glu Asn Phe
 65                  70                  75                  80

Gly Cys Gly Ser Ser Arg Glu Gly Ala Pro Trp Ala Leu Thr Asp Tyr
                 85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 21
<211> LENGTH: 201
<212> TYPE: PRT
<213> ORGANISM: Artificial Sequence
<220> FEATURE:
<223> OTHER INFORMATION: Synthesized - Modified LeuD (L31A H88V)

<400> SEQUENCE: 21

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
 65                  70                  75                  80

Gly Cys Gly Ser Ser Arg Glu Val Ala Pro Trp Ala Leu Thr Asp Tyr
                 85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 22

<211> LENGTH: 201
<212> TYPE: PRT
<213> ORGANISM: Artificial Sequence
<220> FEATURE:
<223> OTHER INFORMATION: Synthesized - Modified LeuD (L31A H88S)

<400> SEQUENCE: 22

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ala Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 23
<211> LENGTH: 201
<212> TYPE: PRT
<213> ORGANISM: Artificial Sequence
<220> FEATURE:
<223> OTHER INFORMATION: Synthesized - Modified LeuD (L31G)

<400> SEQUENCE: 23

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu 115                 120                 125
Val Asp Glu Leu Phe Ala Leu Val Lys Ala Asn Pro Gly Ile His Phe
        130                 135                 140
Asp Val Asp Leu Glu Ala Gln Glu Val Lys Ala Gly Glu Lys Thr Tyr
145                 150                 155                 160
Arg Phe Thr Ile Asp Ala Phe Arg Arg His Cys Met Met Asn Gly Leu
                165                 170                 175
Asp Ser Ile Gly Leu Thr Leu Gln His Asp Asp Ala Ile Ala Ala Tyr
            180                 185                 190
Glu Ala Lys Gln Pro Ala Phe Met Asn
        195                 200

<210> SEQ ID NO 24
<211> LENGTH: 201
<212> TYPE: PRT
<213> ORGANISM: Artificial Sequence
<220> FEATURE:
<223> OTHER INFORMATION: Synthesized - Modified LeuD (L31G H88A)

<400> SEQUENCE: 24

Met Ala Glu Lys Phe Ile Lys His Thr Gly Leu Val Val Pro Leu Asp
1               5                   10                  15
Ala Ala Asn Val Asp Thr Asp Ala Ile Ile Pro Lys Gln Phe Gly Gln
            20                  25                  30
Lys Val Thr Arg Thr Gly Phe Gly Ala His Leu Phe Asn Asp Trp Arg
        35                  40                  45
Phe Leu Asp Glu Lys Gly Gln Gln Pro Asn Pro Asp Phe Val Leu Asn
50                  55                  60
Phe Pro Gln Tyr Gln Gly Ala Ser Ile Leu Leu Ala Arg Glu Asn Phe
65                  70                  75                  80
Gly Cys Gly Ser Ser Arg Glu Ala Ala Pro Trp Ala Leu Thr Asp Tyr
                85                  90                  95
Gly Phe Lys Val Val Ile Ala Pro Ser Phe Ala Asp Ile Phe Tyr Gly
            100                 105                 110
Asn Ser Phe Asn Asn Gln Leu Leu Pro Val Lys Leu Ser Asp Ala Glu
        115                 120                 125
Val Asp Glu Leu Phe Ala Leu Val Lys Ala Asn Pro Gly Ile His Phe
    130                 135                 140
Asp Val Asp Leu Glu Ala Gln Glu Val Lys Ala Gly Glu Lys Thr Tyr
145                 150                 155                 160
Arg Phe Thr Ile Asp Ala Phe Arg Arg His Cys Met Met Asn Gly Leu
                165                 170                 175
Asp Ser Ile Gly Leu Thr Leu Gln His Asp Asp Ala Ile Ala Ala Tyr
            180                 185                 190
Glu Ala Lys Gln Pro Ala Phe Met Asn
        195                 200

<210> SEQ ID NO 25
<211> LENGTH: 201
<212> TYPE: PRT
<213> ORGANISM: Artificial Sequence
<220> FEATURE:
<223> OTHER INFORMATION: Synthesized - Modified LeuD (L31G H88G)

<400> SEQUENCE: 25

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 26
<211> LENGTH: 201
<212> TYPE: PRT
<213> ORGANISM: Artificial Sequence
<220> FEATURE:
<223> OTHER INFORMATION: Synthesized - Modified LeuD (L31G H88V)

<400> SEQUENCE: 26

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 27
<211> LENGTH: 201
<212> TYPE: PRT
<213> ORGANISM: Artificial Sequence
<220> FEATURE:
<223> OTHER INFORMATION: Synthesized - Modified LeuD( L31G H88S)

<400> SEQUENCE: 27

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Gly Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
            85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 28
<211> LENGTH: 201
<212> TYPE: PRT
<213> ORGANISM: Artificial Sequence
<220> FEATURE:
<223> OTHER INFORMATION: Synthesized - Modified LeuD (L31V)

<400> SEQUENCE: 28

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
            85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
            165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 29
<211> LENGTH: 201
<212> TYPE: PRT
<213> ORGANISM: Artificial Sequence
<220> FEATURE:
<223> OTHER INFORMATION: Synthesized - Modified LeuD (L31V H88A)

<400> SEQUENCE: 29

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
        50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
            85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
            165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 30
<211> LENGTH: 201
<212> TYPE: PRT
<213> ORGANISM: Artificial Sequence -continued

```
<220> FEATURE:
<223> OTHER INFORMATION: Synthesized - Modified LeuD (L31V H88G)

<400> SEQUENCE: 30

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 31
<211> LENGTH: 201
<212> TYPE: PRT
<213> ORGANISM: Artificial Sequence
<220> FEATURE:
<223> OTHER INFORMATION: Synthesized - Modified LeuD (L31V H88V)

<400> SEQUENCE: 31

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
```

```
            130                 135                 140
Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 32
<211> LENGTH: 201
<212> TYPE: PRT
<213> ORGANISM: Artificial Sequence
<220> FEATURE:
<223> OTHER INFORMATION: Synthesized - Modified LeuD (L31V H88S)

<400> SEQUENCE: 32

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Val Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 33
<211> LENGTH: 201
<212> TYPE: PRT
<213> ORGANISM: Artificial Sequence
<220> FEATURE:
<223> OTHER INFORMATION: Synthesized - Modified LeuD (L31S)

<400> SEQUENCE: 33

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30
```

```
Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
        50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 34
<211> LENGTH: 201
<212> TYPE: PRT
<213> ORGANISM: Artificial Sequence
<220> FEATURE:
<223> OTHER INFORMATION: Synthesized - Modified LeuD (L31S H88A)

<400> SEQUENCE: 34

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
            35                  40                  45

Phe Leu Asp Glu Lys Gly Gln Gln Pro Asn Pro Asp Phe Val Leu Asn
        50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ala Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
        130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190
```

Glu Ala Lys Gln Pro Ala Phe Met Asn
            195                 200

<210> SEQ ID NO 35
<211> LENGTH: 201
<212> TYPE: PRT
<213> ORGANISM: Artificial Sequence
<220> FEATURE:
<223> OTHER INFORMATION: Synthesized - Modified LeuD (L31S H88G)

<400> SEQUENCE: 35

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Gly Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
            195                 200

<210> SEQ ID NO 36
<211> LENGTH: 201
<212> TYPE: PRT
<213> ORGANISM: Artificial Sequence
<220> FEATURE:
<223> OTHER INFORMATION: Synthesized - Modified LeuD (L31S H88V)

<400> SEQUENCE: 36

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Val Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 37
<211> LENGTH: 201
<212> TYPE: PRT
<213> ORGANISM: Artificial Sequence
<220> FEATURE:
<223> OTHER INFORMATION: Synthesized - Modified LeuD (L31S H88S)

<400> SEQUENCE: 37

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Ser Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu Ser Ala Pro Trp Ala Leu Thr Asp Tyr
                85                  90                  95

Gly Phe Lys Val Val Ile Ala Pro Ser Phe Ala Asp Ile Phe Tyr Gly
                100                 105                 110

Asn Ser Phe Asn Asn Gln Leu Leu Pro Val Lys Leu Ser Asp Ala Glu
            115                 120                 125

Val Asp Glu Leu Phe Ala Leu Val Lys Ala Asn Pro Gly Ile His Phe
130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 38
<211> LENGTH: 30
<212> TYPE: PRT
<213> ORGANISM: Artificial Sequence
<220> FEATURE:
<223> OTHER INFORMATION: Synthesized - Variable Length C-Terminal
      Peptide

```
<220> FEATURE:
<221> NAME/KEY: MISC_FEATURE
<222> LOCATION: (1)..(30)
<223> OTHER INFORMATION: Amino acids designated "Xaa" can be any
      naturally occurring amino acid.  At least two of the amino acids
      designated "Xaa" at positions 1-30 must be present.  Up to
      twenty-eight of the amino acids designated "Xaa" at positions 1-30
      may be absent.

<400> SEQUENCE: 38

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

<210> SEQ ID NO 39
<211> LENGTH: 10
<212> TYPE: PRT
<213> ORGANISM: Artificial Sequence
<220> FEATURE:
<223> OTHER INFORMATION: Synthesized - Variable Length C-Terminal
      Peptide
<220> FEATURE:
<221> NAME/KEY: MISC_FEATURE
<222> LOCATION: (1)..(10)
<223> OTHER INFORMATION: Amino acids designated "Xaa" can be any
      naturally occurring amino acid.  At least two of the amino acids
      designated "Xaa" at positions 1-10 must be present.  Up to eight
      of the amino acids designated "Xaa" at positions 1-10 may be
      absent.

<400> SEQUENCE: 39

Xaa Xaa Xaa Xaa Xaa Xaa Xaa Xaa Xaa Xaa
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthesized - Non-Variable C-Terminal Peptide

<400> SEQUENCE: 40

Ser Ser His His His His His His Ser Ser
1               5                   10

<210> SEQ ID NO 41
<211> LENGTH: 476
<212> TYPE: PRT
<213> ORGANISM: Artificial Sequence
<220> FEATURE:
<223> OTHER INFORMATION: Synthesized - LeuC' Subunit with C-Terminal
      Peptide

<400> SEQUENCE: 41

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Val Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
        50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
```

```
                85                  90                  95
Leu Tyr Asp Leu Asn His Pro Tyr Gln Gly Ile Val His Val Met Gly
            100                 105                 110
Pro Glu Gln Gly Val Thr Leu Pro Gly Met Thr Ile Val Cys Gly Asp
            115                 120                 125
Ser His Thr Ala Thr His Gly Ala Phe Gly Ala Leu Ala Phe Gly Ile
            130                 135                 140
Gly Thr Ser Glu Val Glu His Val Leu Ala Thr Gln Thr Leu Lys Gln
145                 150                 155                 160
Gly Arg Ala Lys Thr Met Lys Ile Glu Val Gln Gly Lys Ala Ala Pro
                165                 170                 175
Gly Ile Thr Ala Lys Asp Ile Val Leu Ala Ile Ile Gly Lys Thr Gly
            180                 185                 190
Ser Ala Gly Gly Thr Gly His Val Val Glu Phe Cys Gly Glu Ala Ile
            195                 200                 205
Arg Asp Leu Ser Met Glu Gly Arg Met Thr Leu Cys Asn Met Ala Ile
210                 215                 220
Glu Met Gly Ala Lys Ala Gly Leu Val Ala Pro Asp Glu Thr Thr Phe
225                 230                 235                 240
Asn Tyr Val Lys Gly Arg Leu His Ala Pro Lys Gly Lys Asp Phe Asp
                245                 250                 255
Asp Ala Val Ala Tyr Trp Lys Thr Leu Gln Thr Asp Glu Gly Ala Thr
            260                 265                 270
Phe Asp Thr Val Val Thr Leu Gln Ala Glu Glu Ile Ser Pro Gln Val
            275                 280                 285
Thr Trp Gly Thr Asn Pro Gly Gln Val Ile Ser Val Asn Asp Asn Ile
290                 295                 300
Pro Asp Pro Ala Ser Phe Ala Asp Pro Val Glu Arg Ala Ser Ala Glu
305                 310                 315                 320
Lys Ala Leu Ala Tyr Met Gly Leu Lys Pro Gly Ile Pro Leu Thr Glu
                325                 330                 335
Val Ala Ile Asp Lys Val Phe Ile Gly Ser Cys Thr Asn Ser Arg Ile
            340                 345                 350
Glu Asp Leu Arg Ala Ala Glu Ile Ala Lys Gly Arg Lys Val Ala
            355                 360                 365
Pro Gly Val Gln Ala Leu Val Val Pro Gly Ser Gly Pro Val Lys Ala
            370                 375                 380
Gln Ala Glu Ala Glu Gly Leu Asp Lys Ile Phe Ile Glu Ala Gly Phe
385                 390                 395                 400
Glu Trp Arg Leu Pro Gly Cys Ser Met Cys Leu Ala Met Asn Asn Asp
                405                 410                 415
Arg Leu Asn Pro Gly Glu Arg Cys Ala Ser Thr Ser Asn Arg Asn Phe
            420                 425                 430
Glu Gly Arg Gln Gly Arg Gly Arg Thr His Leu Val Ser Pro Ala
            435                 440                 445
Met Ala Ala Ala Ala Val Thr Gly His Phe Ala Asp Ile Arg Asn
450                 455                 460
Ile Lys Ser Ser His His His His His Ser Ser
465                 470                 475

<210> SEQ ID NO 42
<211> LENGTH: 479
<212> TYPE: PRT
<213> ORGANISM: Artificial Sequence
```

<220> FEATURE:
<223> OTHER INFORMATION: Synthesized - LeuC' Subunit with N-Terminal Peptide

<400> SEQUENCE: 42

```
Met Gly Ser Ser His His His His His His Ser Ser Gly Met Ala Lys
1               5                   10                  15

Thr Leu Tyr Glu Lys Leu Phe Asp Ala His Val Val Tyr Glu Ala Glu
            20                  25                  30

Asn Glu Thr Pro Leu Leu Tyr Ile Asp Arg His Leu His Glu Val
        35                  40                  45

Thr Ser Pro Gln Ala Phe Asp Gly Leu Arg Ala His Gly Arg Pro Val
50                  55                  60

Arg Gln Pro Gly Lys Thr Phe Ala Thr Met Asp His Asn Val Ser Thr
65                  70                  75                  80

Gln Thr Lys Asp Ile Asn Ala Cys Gly Glu Met Ala Arg Ile Gln Met
                85                  90                  95

Gln Glu Leu Ile Lys Asn Cys Lys Glu Phe Gly Val Glu Leu Tyr Asp
                100                 105                 110

Leu Asn His Pro Tyr Gln Gly Ile Val His Val Met Gly Pro Glu Gln
            115                 120                 125

Gly Val Thr Leu Pro Gly Met Thr Ile Val Cys Gly Asp Ser His Thr
130                 135                 140

Ala Thr His Gly Ala Phe Gly Ala Leu Ala Phe Gly Ile Gly Thr Ser
145                 150                 155                 160

Glu Val Glu His Val Leu Ala Thr Gln Thr Leu Lys Gln Gly Arg Ala
                165                 170                 175

Lys Thr Met Lys Ile Glu Val Gln Gly Lys Ala Ala Pro Gly Ile Thr
                180                 185                 190

Ala Lys Asp Ile Val Leu Ala Ile Ile Gly Lys Thr Gly Ser Ala Gly
            195                 200                 205

Gly Thr Gly His Val Val Glu Phe Cys Gly Glu Ala Ile Arg Asp Leu
210                 215                 220

Ser Met Glu Gly Arg Met Thr Leu Cys Asn Met Ala Ile Glu Met Gly
225                 230                 235                 240

Ala Lys Ala Gly Leu Val Ala Pro Asp Glu Thr Thr Phe Asn Tyr Val
                245                 250                 255

Lys Gly Arg Leu His Ala Pro Lys Gly Lys Asp Phe Asp Asp Ala Val
                260                 265                 270

Ala Tyr Trp Lys Thr Leu Gln Thr Asp Glu Gly Ala Thr Phe Asp Thr
            275                 280                 285

Val Val Thr Leu Gln Ala Glu Glu Ile Ser Pro Gln Val Thr Trp Gly
290                 295                 300

Thr Asn Pro Gly Gln Val Ile Ser Val Asn Asp Asn Ile Pro Asp Pro
305                 310                 315                 320

Ala Ser Phe Ala Asp Pro Val Glu Arg Ala Ser Ala Glu Lys Ala Leu
                325                 330                 335

Ala Tyr Met Gly Leu Lys Pro Gly Ile Pro Leu Thr Glu Val Ala Ile
                340                 345                 350

Asp Lys Val Phe Ile Gly Ser Cys Thr Asn Ser Arg Ile Glu Asp Leu
            355                 360                 365

Arg Ala Ala Ala Glu Ile Ala Lys Gly Arg Lys Val Ala Pro Gly Val
370                 375                 380

Gln Ala Leu Val Val Pro Gly Ser Gly Pro Val Lys Ala Gln Ala Glu
```

```
385                 390                 395                 400
Ala Glu Gly Leu Asp Lys Ile Phe Ile Glu Ala Gly Phe Glu Trp Arg
            405                 410                 415

Leu Pro Gly Cys Ser Met Cys Leu Ala Met Asn Asn Asp Arg Leu Asn
            420                 425                 430

Pro Gly Glu Arg Cys Ala Ser Thr Ser Asn Arg Asn Phe Glu Gly Arg
        435                 440                 445

Gln Gly Arg Gly Gly Arg Thr His Leu Val Ser Pro Ala Met Ala Ala
    450                 455                 460

Ala Ala Ala Val Thr Gly His Phe Ala Asp Ile Arg Asn Ile Lys
465                 470                 475
```